(12) United States Patent
Germain et al.

(10) Patent No.: US 11,207,119 B2
(45) Date of Patent: Dec. 28, 2021

(54) ARTHROSCOPIC DEVICES AND METHODS

(71) Applicant: RELIGN Corporation, Cupertino, CA (US)

(72) Inventors: Aaron Germain, San Jose, CA (US); Simon Malkevich, Gilroy, CA (US); Steffan Benamou, Morgan Hill, CA (US); Kyle Klein, San Jose, CA (US); Ben Poser, Campbell, CA (US)

(73) Assignee: Relign Corporation, Campbell, CA (US)

( * ) Notice: Subject to any disclaimer, the term of this patent is extended or adjusted under 35 U.S.C. 154(b) by 1051 days.

(21) Appl. No.: 15/454,690

(22) Filed: Mar. 9, 2017

(65) Prior Publication Data
US 2017/0258512 A1 Sep. 14, 2017

Related U.S. Application Data

(60) Provisional application No. 62/308,743, filed on Mar. 15, 2016, provisional application No. 62/308,705, (Continued)

(51) Int. Cl.
*A61B 18/08* (2006.01)
*A61B 17/32* (2006.01)
(Continued)

(52) U.S. Cl.
CPC ........ *A61B 18/082* (2013.01); *A61B 17/1615* (2013.01); *A61B 17/1626* (2013.01); (Continued)

(58) Field of Classification Search
CPC .. A61B 2017/00017; A61B 2017/0023; A61B 2017/0046; A61B 2017/00477; (Continued)

(56) References Cited

U.S. PATENT DOCUMENTS

| | | |
|---|---|---|
| 2,513,564 A | 7/1950 | Ingwersen |
| 2,514,545 A | 7/1950 | Ingwersen |

(Continued)

FOREIGN PATENT DOCUMENTS

| | | |
|---|---|---|
| CN | 200998857 Y | 1/2008 |
| CN | 101507635 A | 8/2009 |

(Continued)

OTHER PUBLICATIONS

International Search Report and Written Opinion dated May 22, 2017 for International PCT Patent Application No. PCT/US2017/021675.

(Continued)

*Primary Examiner* — Ronald Hupczey, Jr.
*Assistant Examiner* — Bradford C. Blaise
(74) *Attorney, Agent, or Firm* — Schwegman Lundberg & Woessner, P.A.

(57) ABSTRACT

An arthroscopic system includes a re-useable, sterilizable handle integrated with a single umbilical cable or conduit. The single umbilical cable or conduit carries electrical power from a power and/or control console to the handle for operating both a motor drive unit within the handle and delivering the RF power to a disposable RF probe or cutter which may be detachably connected to the handle. The RF power delivered to the handle and on to the probe or cutter is typically bi-polar, where the handle includes first and second electrical bi-polar contacts that couple to corresponding bi-polar electrical contacts on a hub of the disposable RF probe or cutter is connected to the handle.

14 Claims, 25 Drawing Sheets

Related U.S. Application Data filed on Mar. 15, 2016, provisional application No. 62/307,229, filed on Mar. 11, 2016.

(51) Int. Cl.

| | | |
|---|---|---|
| *A61B 17/16* | (2006.01) | |
| *A61B 18/14* | (2006.01) | |
| *A61B 17/3207* | (2006.01) | |
| *A61B 17/00* | (2006.01) | |
| *A61B 18/00* | (2006.01) | |

(52) U.S. Cl.
CPC .... *A61B 17/1633* (2013.01); *A61B 17/32002* (2013.01); *A61B 17/320783* (2013.01); *A61B 18/148* (2013.01); *A61B 18/1482* (2013.01); A61B 17/320016 (2013.01); A61B 2017/00017 (2013.01); A61B 2017/0023 (2013.01); A61B 2017/0088 (2013.01); A61B 2017/320024 (2013.01); A61B 2017/320028 (2013.01); A61B 2018/0091 (2013.01); A61B 2018/00196 (2013.01); A61B 2018/00202 (2013.01); A61B 2018/00208 (2013.01); A61B 2018/00214 (2013.01); A61B 2018/00601 (2013.01); A61B 2018/1472 (2013.01); A61B 2018/1475 (2013.01)

(58) Field of Classification Search
CPC ............ A61B 2017/0088; A61B 17/16; A61B 17/1615; A61B 17/1626; A61B 17/1633; A61B 17/320016; A61B 17/32002; A61B 17/320783; A61B 2017/320024; A61B 2017/320028; A61B 2017/320032; A61B 2017/320791; A61B 2018/00184; A61B 2018/00196; A61B 2018/00202; A61B 2018/00208; A61B 2018/00607; A61B 2018/0091; A61B 18/148; A61B 18/1482
See application file for complete search history.

(56) References Cited

U.S. PATENT DOCUMENTS

| | | |
|---|---|---|
| 2,625,625 A | 1/1953 | Ingwersen |
| 2,689,895 A | 9/1954 | Ingwersen |
| 3,611,023 A | 10/1971 | Jesse et al. |
| 3,838,242 A | 9/1974 | Goucher |
| 3,848,211 A | 11/1974 | Russell |
| 3,868,614 A | 2/1975 | Riendeau |
| 3,899,829 A | 8/1975 | Storm et al. |
| 3,903,891 A | 9/1975 | Brayshaw |
| 3,945,375 A | 3/1976 | Banko |
| 4,060,088 A | 11/1977 | Morrison, Jr. et al. |
| 4,272,687 A | 6/1981 | Borkan |
| 4,781,175 A | 11/1988 | McGreevy et al. |
| 4,815,462 A | 3/1989 | Clark |
| 4,895,146 A | 1/1990 | Draenert |
| 4,936,842 A | 6/1990 | D'Amelio et al. |
| 4,977,346 A | 12/1990 | Gibson et al. |
| 5,012,495 A | 4/1991 | Munroe et al. |
| 5,122,138 A | 6/1992 | Manwaring |
| 5,207,675 A | 5/1993 | Canady |
| 5,256,138 A | 10/1993 | Burek et al. |
| 5,281,217 A | 1/1994 | Edwards et al. |
| 5,433,721 A | 7/1995 | Hooven et al. |
| 5,449,356 A | 9/1995 | Walbrink et al. |
| 5,490,854 A | 2/1996 | Fisher et al. |
| 5,520,634 A | 5/1996 | Fox et al. |
| 5,641,251 A | 6/1997 | Leins et al. |
| 5,669,907 A | 9/1997 | Platt, Jr. et al. |
| 5,683,366 A | 11/1997 | Eggers et al. |
| 5,702,420 A | 12/1997 | Sterling et al. |
| 5,720,745 A | 2/1998 | Farin et al. |
| 5,759,185 A | 6/1998 | Grinberg |
| 5,766,195 A | 6/1998 | Nobles |
| 5,776,092 A | 7/1998 | Farin et al. |
| 5,810,809 A | 9/1998 | Rydell |
| 5,823,971 A | 10/1998 | Robinson et al. |
| 5,839,897 A | 11/1998 | Bordes |
| 5,849,010 A | 12/1998 | Wurzer et al. |
| 5,857,995 A | 1/1999 | Thomas et al. |
| 5,873,855 A | 2/1999 | Eggers et al. |
| 5,888,198 A | 3/1999 | Eggers et al. |
| 5,891,095 A | 4/1999 | Eggers et al. |
| 5,904,681 A | 5/1999 | West, Jr. |
| 5,913,867 A | 6/1999 | Dion |
| 5,954,731 A | 9/1999 | Yoon |
| 5,957,884 A | 9/1999 | Hooven |
| 5,964,752 A | 10/1999 | Stone |
| 5,989,248 A | 11/1999 | Tu et al. |
| 6,007,553 A | 12/1999 | Hellenkamp et al. |
| 6,013,075 A | 1/2000 | Avramenko et al. |
| 6,013,076 A | 1/2000 | Goble et al. |
| 6,024,733 A | 2/2000 | Eggers et al. |
| 6,032,674 A | 3/2000 | Eggers et al. |
| 6,039,736 A | 3/2000 | Platt, Jr. |
| 6,056,747 A | 5/2000 | Saadat et al. |
| 6,066,134 A | 5/2000 | Eggers et al. |
| 6,099,523 A | 8/2000 | Kim et al. |
| 6,142,992 A | 11/2000 | Cheng et al. |
| 6,149,620 A | 11/2000 | Baker et al. |
| 6,159,208 A | 12/2000 | Hovda et al. |
| 6,193,715 B1 | 2/2001 | Wrublewski et al. |
| 6,225,883 B1 | 5/2001 | Wellner et al. |
| 6,235,020 B1 | 5/2001 | Cheng et al. |
| 6,238,391 B1 | 5/2001 | Olsen et al. |
| 6,261,241 B1 | 7/2001 | Burbank et al. |
| 6,296,636 B1 | 10/2001 | Cheng et al. |
| 6,332,886 B1 | 12/2001 | Green et al. |
| 6,348,051 B1 | 2/2002 | Farin et al. |
| 6,394,956 B1 | 5/2002 | Chandrasekaran et al. |
| 6,413,256 B1 | 7/2002 | Truckai et al. |
| 6,419,674 B1 | 7/2002 | Bowser et al. |
| 6,443,948 B1 | 9/2002 | Suslov |
| 6,475,215 B1 | 11/2002 | Tanrisever |
| 6,538,549 B1 | 3/2003 | Renne et al. |
| 6,579,289 B2 | 6/2003 | Schnitzler |
| 6,610,059 B1 | 8/2003 | West et al. |
| 6,629,986 B1 | 10/2003 | Ross et al. |
| 6,632,220 B1 | 10/2003 | Eggers et al. |
| 6,656,195 B2 | 12/2003 | Peters et al. |
| 6,669,694 B2 | 12/2003 | Shadduck |
| 6,720,856 B1 | 4/2004 | Pellon et al. |
| 6,780,178 B2 | 8/2004 | Palanker et al. |
| 6,783,533 B2 | 8/2004 | Green et al. |
| 6,821,275 B2 | 11/2004 | Truckai et al. |
| 6,827,725 B2 | 12/2004 | Batchelor et al. |
| 6,837,884 B2 | 1/2005 | Woloszko |
| 6,837,888 B2 | 1/2005 | Ciarrocca et al. |
| 6,890,332 B2 | 5/2005 | Truckai et al. |
| 6,902,564 B2 | 6/2005 | Morgan et al. |
| 6,979,332 B2 | 12/2005 | Adams |
| 7,087,054 B2 | 8/2006 | Truckai et al. |
| 7,112,200 B2 | 9/2006 | Cucin |
| 7,150,747 B1 | 12/2006 | McDonald et al. |
| 7,220,261 B2 | 5/2007 | Truckai et al. |
| 7,309,849 B2 | 12/2007 | Truckai et al. |
| 7,549,989 B2 | 6/2009 | Morgan et al. |
| 7,674,263 B2 | 3/2010 | Ryan |
| 7,678,069 B1 | 3/2010 | Baker et al. |
| 7,713,269 B2 | 5/2010 | Auge et al. |
| 7,717,710 B2 | 5/2010 | Danger et al. |
| 7,744,595 B2 | 6/2010 | Truckai et al. |
| 7,771,422 B2 | 8/2010 | Auge et al. |
| 7,819,861 B2 | 10/2010 | Auge et al. |
| 7,819,864 B2 | 10/2010 | Morgan et al. |
| 7,955,331 B2 | 6/2011 | Truckai et al. |
| 8,012,153 B2 | 9/2011 | Woloszko et al. |
| 8,016,823 B2 | 9/2011 | Shadduck |
| 8,062,319 B2 | 11/2011 | O'Quinn et al. |
| 8,075,555 B2 | 12/2011 | Truckai et al. |
| 8,192,424 B2 | 6/2012 | Woloszko |
| 8,192,428 B2 | 6/2012 | Truckai et al. |

(56) References Cited

U.S. PATENT DOCUMENTS

| | | |
|---|---|---|
| 8,197,483 B2 | 6/2012 | Faulhaber |
| 8,221,404 B2 | 7/2012 | Truckai |
| 8,323,280 B2 | 12/2012 | Germain et al. |
| 8,333,763 B2 | 12/2012 | Truckai et al. |
| 9,005,203 B2 | 4/2015 | Nelson et al. |
| 9,179,923 B2 | 11/2015 | Gubellini et al. |
| 9,504,521 B2 | 11/2016 | Deutmeyer et al. |
| 9,585,675 B1 | 3/2017 | Germain et al. |
| 9,603,656 B1 | 3/2017 | Aaron et al. |
| 10,595,889 B2 | 3/2020 | Germain et al. |
| 2003/0014051 A1 | 1/2003 | Woloszko |
| 2003/0083681 A1 | 5/2003 | Moutafis et al. |
| 2003/0125727 A1 | 7/2003 | Truckai et al. |
| 2003/0163135 A1 | 8/2003 | Hathaway |
| 2004/0044341 A1 | 3/2004 | Truckai et al. |
| 2004/0167427 A1 | 8/2004 | Quick et al. |
| 2005/0015085 A1 | 1/2005 | McClurken et al. |
| 2005/0075630 A1 | 4/2005 | Truckai et al. |
| 2005/0228372 A1 | 10/2005 | Truckai et al. |
| 2006/0058782 A1 | 3/2006 | Truckai et al. |
| 2006/0074345 A1 | 4/2006 | Hibner |
| 2006/0178670 A1 | 8/2006 | Woloszko et al. |
| 2006/0224154 A1 | 10/2006 | Shadduck et al. |
| 2007/0213704 A1 | 9/2007 | Truckai et al. |
| 2008/0003255 A1 | 1/2008 | Kerr et al. |
| 2008/0027448 A1 | 1/2008 | Raus et al. |
| 2008/0103494 A1 | 5/2008 | Rioux et al. |
| 2008/0188848 A1 | 8/2008 | Deutmeyer et al. |
| 2008/0208249 A1 | 8/2008 | Blain et al. |
| 2008/0249533 A1 | 10/2008 | Godin |
| 2008/0249553 A1 | 10/2008 | Gruber et al. |
| 2009/0076498 A1 | 3/2009 | Saadat et al. |
| 2009/0209946 A1 | 8/2009 | Swayze et al. |
| 2009/0248019 A1 | 10/2009 | Falkenstein et al. |
| 2009/0270849 A1 | 10/2009 | Truckai et al. |
| 2010/0057078 A1 | 3/2010 | Arts et al. |
| 2010/0087816 A1 | 4/2010 | Roy |
| 2010/0100091 A1 | 4/2010 | Truckai |
| 2010/0305565 A1 | 12/2010 | Truckai et al. |
| 2011/0160723 A1 | 6/2011 | Tullis et al. |
| 2011/0282373 A1 | 11/2011 | Chekan et al. |
| 2011/0301578 A1* | 12/2011 | Muniz-Medina ............ A61B 18/1402 606/1 |
| 2012/0029545 A1 | 2/2012 | Nelson et al. |
| 2012/0209112 A2 | 8/2012 | Patel et al. |
| 2012/0245580 A1 | 9/2012 | Germain et al. |
| 2012/0310256 A1 | 12/2012 | Brisson |
| 2012/0330292 A1 | 12/2012 | Shadduck et al. |
| 2013/0041360 A1 | 2/2013 | Farritor et al. |
| 2013/0122461 A1 | 5/2013 | Shioiri |
| 2013/0172870 A1 | 7/2013 | Germain et al. |
| 2013/0253498 A1 | 9/2013 | Germain et al. |
| 2013/0267937 A1 | 10/2013 | Shadduck et al. |
| 2013/0296847 A1 | 11/2013 | Germain et al. |
| 2013/0296849 A1 | 11/2013 | Germain et al. |
| 2013/0317492 A1 | 11/2013 | Truckai et al. |
| 2013/0317493 A1 | 11/2013 | Truckai et al. |
| 2013/0331833 A1 | 12/2013 | Bloom |
| 2014/0005680 A1 | 1/2014 | Shelton, IV et al. |
| 2014/0012238 A1 | 1/2014 | Chen et al. |
| 2014/0025046 A1 | 1/2014 | Williams et al. |
| 2014/0100567 A1 | 4/2014 | Edwards et al. |
| 2014/0114300 A1 | 4/2014 | Orczy-Timko et al. |
| 2014/0336643 A1 | 11/2014 | Orczy-Timko et al. |
| 2015/0209061 A1 | 7/2015 | Johnson et al. |
| 2015/0272569 A1 | 10/2015 | Leimbach et al. |
| 2016/0081737 A1 | 3/2016 | Germain et al. |
| 2016/0113706 A1 | 4/2016 | Truckai et al. |
| 2016/0157916 A1 | 6/2016 | Germain et al. |
| 2016/0346036 A1 | 12/2016 | Orczy-Timko et al. |
| 2017/0027599 A1 | 2/2017 | Bek et al. |
| 2017/0128083 A1 | 5/2017 | Germain et al. |
| 2017/0258519 A1 | 9/2017 | Germain et al. |
| 2017/0290602 A1 | 10/2017 | Germain et al. |
| 2019/0008537 A1 | 1/2019 | Kirstgen et al. |
| 2019/0008541 A1 | 1/2019 | Norton et al. |

FOREIGN PATENT DOCUMENTS

| | | |
|---|---|---|
| CN | 103857354 A | 6/2014 |
| CN | 103948427 | 7/2014 |
| CN | 104487007 | 4/2015 |
| CN | 105377159 | 3/2016 |
| CN | 109561846 A | 4/2019 |
| DE | 102005059864 A1 | 6/2007 |
| EP | 0119405 A1 | 9/1984 |
| EP | 1034747 A1 | 9/2000 |
| EP | 3426140 A1 | 1/2019 |
| JP | 2019509805 A | 4/2019 |
| WO | WO-0053112 A2 | 9/2000 |
| WO | WO-0062685 A1 | 10/2000 |
| WO | WO-0053112 A3 | 12/2000 |
| WO | WO-2007073867 A1 | 7/2007 |
| WO | WO-2014165715 A1 | 10/2014 |
| WO | WO-2015100310 A1 | 7/2015 |
| WO | WO-2017151993 A1 | 9/2017 |
| WO | WO-2017156335 A1 | 9/2017 |
| WO | WO-2017156343 A1 | 9/2017 |
| WO | WO-2017180654 A1 | 10/2017 |
| WO | WO-2019067460 A1 | 4/2019 |

OTHER PUBLICATIONS

International Search Report and Written Opinion dated Aug. 1, 2017 for International PCT Patent Application PCT/US2017/021687.

International Search Report and Written Opinion dated Aug. 22, 2017 for International PCT Patent Application No. PCT/US2017/027053.

Co-pending U.S. Appl. No. 15/421,264, filed Jan. 31, 2017.

Co-pending U.S. Appl. No. 15/449,796, filed Mar. 3, 2017.

Co-pending U.S. Appl. No. 15/599,372, filed May 18, 2017.

European search report dated Nov. 2, 2009 for EP Application No. 01967968.7.

International search report and opinion dated Jul. 15, 2016 for PCT/US2016/027157.

International Search Report and Written Opinion dated May 16, 2017 for International PCT Patent Application No. PCT/US2017/016002.

International search report and written opinion dated May 23, 2012 for PCT/US2012/023390.

International Search Report and Written Opinion dated Nov. 29, 2016 for International Application No. PCT/US2016/058145.

International search report dated Jan. 14, 2002 for PCT/US2001/025409.

Kim, et al. Optical feedbacksignal for ultra short pulse ablation of tissue. Appl. Surface Sci. 1998; 127-129:857-862.

Notice of Allowance dated Jan. 6, 2017 for U.S. Appl. No. 14/960,084.

Notice of Allowance dated Feb. 8, 2017 for U.S. Appl. No. 14/977,256.

Notice of Allowance dated Feb. 16, 2017 for U.S. Appl. No. 15/096,546.

Notice of Allowance dated Dec. 2, 2016 for U.S. Appl. No. 14/977,256.

Notice of Allowance dated Dec. 30, 2016 for U.S. Appl. No. 14/977,256.

Office action dated May 3, 2016 for U.S. Appl. No. 14/960,084.

Office action dated Jul. 28, 2016 for U.S. Appl. No. 14/977,256.

Office Action dated Aug. 18, 2016 for U.S. Appl. No. 14/960,084.

Office action dated Sep. 26, 2016 for U.S. Appl. No. 15/096,546.

Pedowitz, et al. Arthroscopic surgical tools: a source of metal particles and possible joint damage. Arthroscopy. Sep. 2013;29(9):1559-65. doi: 10.1016/j.arthro.2013.05.030. Epub Jul. 30, 2013.

Tucker et al. Histologic characteristics of electrosurgical injuries. J. Am. Assoc. Gyneco. Laproscopy. 1997; 4(2):857-862.

Volpato, et al., Application of Zirconia in Dentistry: Biological, Mechanical and Optical Considerations. Advances in ceramics—electric and magnetic ceramics, bioceramics, ceramics and environment. Sep. 2011.

(56) References Cited

OTHER PUBLICATIONS

Co-pending U.S. Appl. No. 16/789,845, filed Feb. 13, 2020.
European search report and opinion dated Feb. 3, 2020 for EP Application No. 17783001.5.
European search report and opinion dated Oct. 2, 2019 for EP Application No. 17764155.2.
International search report with written opinion dated Jan. 24, 2019 for PCT/US2018/052696.
Notice of Allowance dated Nov. 13, 2019 for U.S. Appl. No. 15/483,940.
Office action dated Aug. 20, 2019 for U.S. Appl. No. 15/483,940.
Partial supplementary European search report and provisional opinion dated Oct. 31, 2019 for EP Application No. 17783001.5.
"Japanese Application Serial No. 2018-547985, Decision of Refusal dated May 18, 2021", with English translation, 6 pages.
"Chinese Application Serial No. 201780029225.1, Response filed May 25, 2021 to Notification of Paying the Restoration Fee dated Dec. 22, 2020", (W/ English Translation of Claims), 24 pgs.
"European Application Serial No. 17764155.2, Response filed Apr. 28, 2020 to Extended European Search Report dated Oct. 2, 1019", 61 pgs.
"International Application Serial No. PCT/US2017/021687, International Preliminary Report on Patentability dated Sep. 20, 2018", 8 pgs.
"Japanese Application Serial No. 2018-547985, Notification of Reasons for Refusal dated Feb. 5, 2021", (W/ English Translation), 8 pgs.
"Japanese Application Serial No. 2018-547985, Response filed Apr. 23, 2021 to Notification of Reasons for Refusal dated Feb. 5, 2021", (W/ English Translation of Claims), 8 pgs.
"Chinese Application Serial No. 201780029225.1, Office Action dated Aug. 4, 2021", with English translation, 29 pages.
"Chinese Application Serial No. 201780029225.1, Response filed Sep. 29, 2021 to Office Action dated Aug. 4, 2021", with English claims, 23 pages.

* cited by examiner

ARTHROSCOPIC DEVICES AND METHODS

CROSS-REFERENCE TO RELATED APPLICATIONS

This application claims priority to Provisional Application No. 62/307,229, filed Mar. 11, 2016, Provisional Application No. 62/308,705, filed Mar. 15, 2016, and Provisional Application No. 62/308,743, filed Mar. 15, 2016, the entire contents of which are incorporated herein in their entirety.

BACKGROUND OF THE INVENTION

1. Field of the Invention

This invention relates to arthroscopic tissue cutting and removal devices by which anatomical tissues may be cut and removed from a joint or other site. More specifically, this invention relates to instruments configured for cutting and removing soft tissue with an electrosurgical device.

In several surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures, and a need had existed for arthroscopic cutters that remove soft tissue rapidly.

Recently, arthroscopic surgical cutters capable of selectively removing both hard tissues and soft tissues have been developed. Such cutters are described in the following US Patent Publications which are commonly assigned with the present application: US20130253498; US20160113706; US20160346036; US20160157916; and US20160081737, the full disclosures of which are incorporated herein by reference.

While very effective, it would be desirable to provide arthroscopic surgical cutters and cutter systems as "reposable" devices with disposable cutting components and reusable, sterilizable handles. Preferably, the handles would incorporate as many of the high value system components as possible. Further preferably, the handle designs would have a minimum number of external connections to simplify sterilization and set-up. Still more preferably, the cutters and systems would allow for bipolar cutting as well as monopolar and mechanical (cutting blade) resection. At least some of these objectives will be met by the inventions described herein.

2. Description of the Background Art

Various surgical systems have been disclosed that include a handpiece and/or motor drive that is coupled to a disposable electrosurgical cutter assembly, including U.S. Pat. Nos. 3,945,375; 4,815,462; 5,810,809; 5,957,884; 6,007,553; 6,629,986 6,827,725; 7,112,200 and 9,504,521. One commercially available RF shaver sold under the tradename DYONICS Bonecutter Electroblade Resector (See, http://www.smith-nephew.com/professional/products/all-products/dyonics-bonecutter-electroblade) utilizes an independent or separate RF electrical cable that carries neither motor power nor electrical signals and couples directly to an exposed part or external surface of the prior art shaver hub. The electrical cable must be routed distally in parallel to a reusable handle. In such a prior art device, the coupling of RF does not extend through the reusable handle. The use of Hall effect sensors for monitoring rotational speed of an inner sleeve relative to an outer sleeve in an electrosurgical cutter is described in US 2016/0346036 and US 2017/0027599, both having a common inventor with the present application. Other commonly assigned published US Patent Applications have been listed above, including US20130253498; US20160113706; US20160346036; US20160157916; and US20160081737.

SUMMARY OF THE INVENTION

In general, arthroscopic systems according to the present invention include a re-useable, sterilizable handle or handpiece integrated with a single umbilical cable or conduit. The single umbilical cable or conduit carries electrical power from a power and/or control console to the handle for operating both a motor drive unit within the handle and for delivering the RF power to a disposable RF probe or cutter which may be detachably connected to the handle. The RF power delivered to the handle and on to the probe or cutter is typically bi-polar, where the handle includes first and second electrical bi-polar contacts that couple to corresponding bi-polar electrical contacts on a hub of the disposable RF probe or cutter that is connected to the handle.

In a first aspect, the present invention provides a disposable bipolar RF probe for use in the presence of an electrically conductive fluid. The probe comprises a shaft including an inner electrically conductive sleeve and an outer electrically conductive sleeve and a hub having a central passage. Opposing polarity regions of the inner and outer electrically conductive sleeves are present, typically exposed, in the central passage, and the opposing polarity regions have a spacing therebetween which inhibits intrusion of the conductive fluid and limits RF or other current flow between said opposing polarity regions when, for example, a distal working end of the probe is immersed in or otherwise in the presence of a conductive fluid during use.

The proximal hub of the disposable bipolar RF probe is typically configured or adapted for detachable coupling to a handle carrying first and second electrical contacts for coupling RF current through the hub to said first and second conductive sleeves. The inner and outer electrically conductive sleeves may be configured to couple RF current flow to respective first and second opposing polarity electrodes in the working end of the probe, and the intrusion of conductive fluid is usually limited sufficiently in the interior and central passage of the hub so that RF current flow to the working end is in presence of the conductive fluid is unimpeded.

In specific examples of the disposable bipolar RF probe, at least a portion of the inner electrically conductive sleeve is rotationally disposed in a bore of the outer electrically conductive sleeve, and said opposing polarity regions are longitudinally spaced apart in the interior of the hub by a distance selected to at least substantially impede or limit RF current flow between said opposing polarity regions during use. The selected distance is usually at least 0.5 inch, often at least 0.6 inch, frequently at least 0.8 inch, and sometimes at least 1 inch, or longer. The inner and outer sleeves are separated by an annular space in the hub of usually less than 0.010 inch, often less than 0.004 inch, and frequently less than 0.002 inch to further minimize fluid intrusion and maximize electrical resistance between said opposing polarity regions.

In a second aspect of the present invention, an arthroscopic treatment system comprises a disposable bipolar RF probe as described above and a handle, where the handle includes a motor drive unit for rotating the second conductive sleeve when the disposable bipolar RF probe is coupled to the hub.

In a third aspect of the present invention, a surgical system comprises a handle carrying a motor drive unit. A disposable RF probe has a proximal hub that detachably couples to the handle, an RF effector, and a component that is driven by the motor drive unit. At least one Hall sensor is carried by or otherwise coupled the motor drive unit to provide signals representative of motor operating parameters. A controller is operatively coupled to the motor and the RF probe by an umbilical conduit that includes (i) an electrical cable for delivering electrical power to the motor, (ii) an RF cable for delivering RF power to the RF effector, and (iii) at least one signal circuit including a signal cable for delivering signals from Hall signals to the controller. Typically, at least one Schmitt trigger operatively coupled to the at least one signal circuit for reducing noise induction therein.

As used herein, the phrase "Hall effect sensor" refers to a transducer or equivalent analog or digital circuitry that varies its output voltage in response to a magnetic field. Typically, the Hall effect sensor operates as an analog transducer, directly outputting a voltage signal induced by the motor drive in the handle to analog or digital circuitry in a controller or other control circuitry in the control console of the present invention for the purposes described in detail below.

As used herein, the phrase "Schmitt trigger" refers to a comparator circuit with hysteresis implemented by applying positive feedback to the noninverting input of a comparator or differential amplifier. It is an analog or digital active circuit which converts an analog input signal to a digital output signal and may be implemented in the control circuitry of the systems of the present invention for the purposes described in detail below.

In exemplary embodiments of the surgical systems of the present invention, a plurality of Hall sensors are carried by or otherwise coupled to the handle and the motor drive unit, where each Hall sensor comprises a signal circuit connected by a signal cable in the umbilical conduit to the controller. A first Schmitt trigger is located in a handle end of each signal circuit and a second Schmitt trigger is located in a controller end of each signal circuit. For example, three Hall sensors may be carried by or otherwise coupled to the handle and the motor drive unit wherein each of the three Hall sensors comprises a signal circuit connected by a signal cable in the umbilical conduit to the controller, and a Schmitt trigger may be located in a handle end of each of the three signal circuits and another Schmitt trigger may be located in a controller end of each of the three signal circuits.

In a fourth aspect of the present invention, a surgical system comprises a handle carrying a motor drive unit including Hall sensors therein. A disposable RF probe has a proximal hub that detachably couples to the handle, and the RF probe has an RF effector and a component that is driven by the motor drive unit. A single umbilical conduit extends from the handle to a control console, and the single conduit includes (i) an electrical cable for delivering electrical power to the motor, (ii) an RF cable for delivering RF power to the RF effector, and (iii) a plurality of signal cables for carrying Hall sensor signals. The surgical system may further comprise a first Schmitt trigger coupled to each signal cable at a handle end thereof and a second Schmitt trigger coupled to each signal cable at a console end thereof.

In a fifth aspect of the present invention, a method of operating an arthroscopic treatment system comprises providing a disposable RF treatment device detachably coupled to a handle that carries a motor drive unit, where the handle is coupled to a control console through a single conduit. Power is delivered to the motor and the RF device through first and second respective electrical cables in the single conduit. A Hall sensor coupled to the motor drive sends motor operating parameter signals to the control console in a signal circuit including an electrical cable in the single conduit. At least one Schmitt trigger in the signal circuit reduces noise induction therein due to the proximity of the first and second electrical cables.

In a sixth aspect of the present invention, an arthroscopic system comprises a probe having a distal bipolar element and a proximal hub having a first polarity electrical contact and a second polarity electrical contact. A handle having a distal cylindrical passageway is configured to removably receive the proximal hub of the probe, and the hub has a first polarity electrical contact and a second polarity electrical contact. The first polarity electrical contact and the second polarity electrical contact on the hub engage the first polarity electrical contact and the second polarity electrical contact in the passageway, and the first and second electrical contacts in the distal passageway of the handle comprise a conductive material which is resistant to alternating current corrosion.

In specific embodiments, the first and second electrical contacts in the distal passageway of the handle may comprise or are plated with a material selected from the group consisting of titanium, gold, silver, platinum, carbon, molybdenum, tungsten, zinc, Inconel, graphite, nickel or a combination thereof. The first and second electrical contacts in the distal passageway of the handle may be axially spaced-apart and exposed on an inner surface of the distal passageway, where the first and second electrical contacts may comprise ring-like contacts which extend circumferentially around at least a portion of the cylindrical passageway, typically extending 360° around the inner surface of the cylindrical passageway. The arthroscopic systems may further comprise a fluid seal between the hub and the cylindrical passageway, where the fluid seal often comprises at least one O-ring disposed on the inner surface of the cylindrical passageway. The fluid seal further may further comprises at least one O-ring disposed on the proximal hub of the probe, and at least one of the O-rings is disposed between the axially spaced apart electrical contacts. Often, at least one O-ring is also disposed proximally of all of the electrical contacts and at least one of the O-rings is disposed distally of all of the electrical contacts.

In other embodiments, the handle carries a motor drive unit with a non-detachable umbilical conduit, where said umbilical conduit carries a plurality of electrical cables. Usually, at least one electrical cable is connected to drive the motor drive unit, at least one cable is connected to the first polarity electrical contact in the passageway, and at least one cable is connected to the second polarity electrical contact in the passageway. The umbilical conduit may further carry one or more electrical cables for signaling and control functions, and the first polarity electrical contact and the second polarity electrical contact on the proximal hub of the probe may comprise spring-loaded elements on an outer surface of the hub.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and removal devices and related methods of use. Several variations of the invention will now be described to provide an overall understanding of the principles of the form, function and methods of use of the devices disclosed herein. In general, the present disclosure provides for an arthroscopic cutter or burr assembly for cutting or abrading bone that is disposable and is configured for detachable coupling to a non-disposable handle and motor drive component. This description of the general principles of this invention is not meant to limit the inventive concepts in the appended claims.

In general, the present invention provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds ranging from 3,000 rpm to 20,000 rpm.

Figure 1:
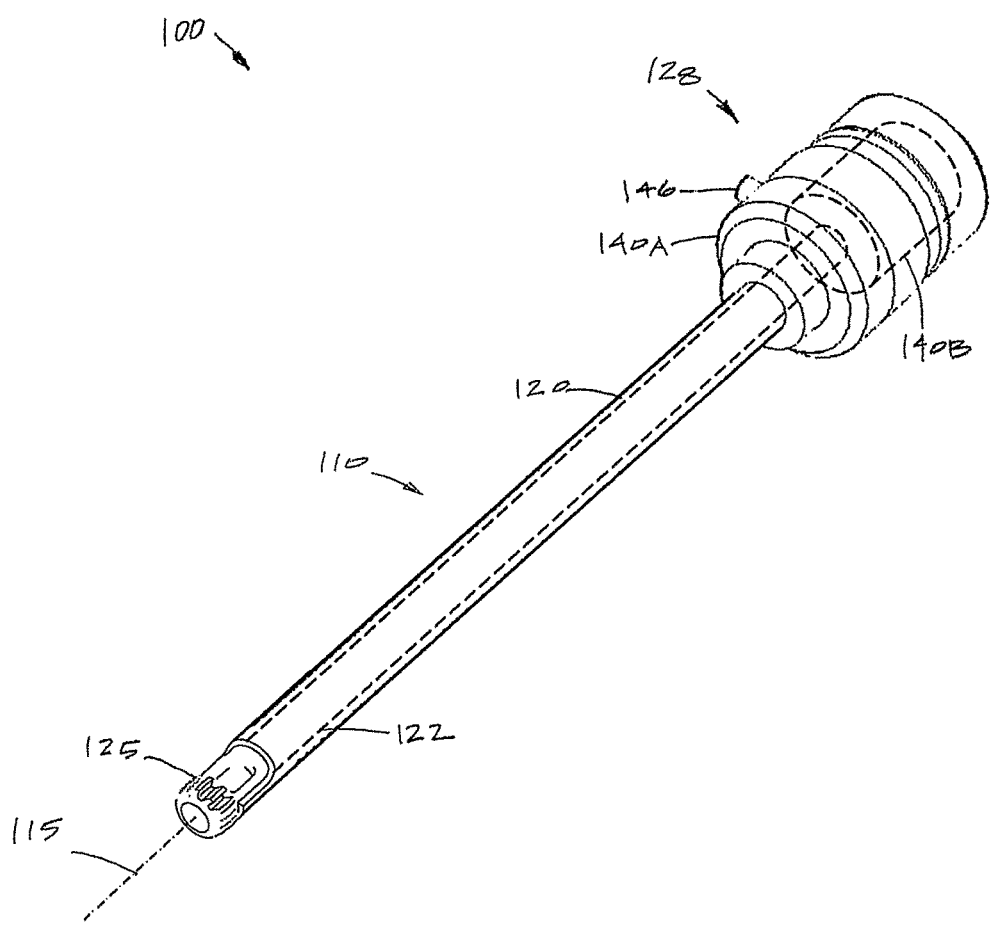
FIG. 1 is a perspective view of a disposable arthroscopic cutter or burr assembly with a ceramic cutting member carried at the distal end of a rotatable inner sleeve with a window in the cutting member proximal to the cutting edges of the burr.
Figure 2:
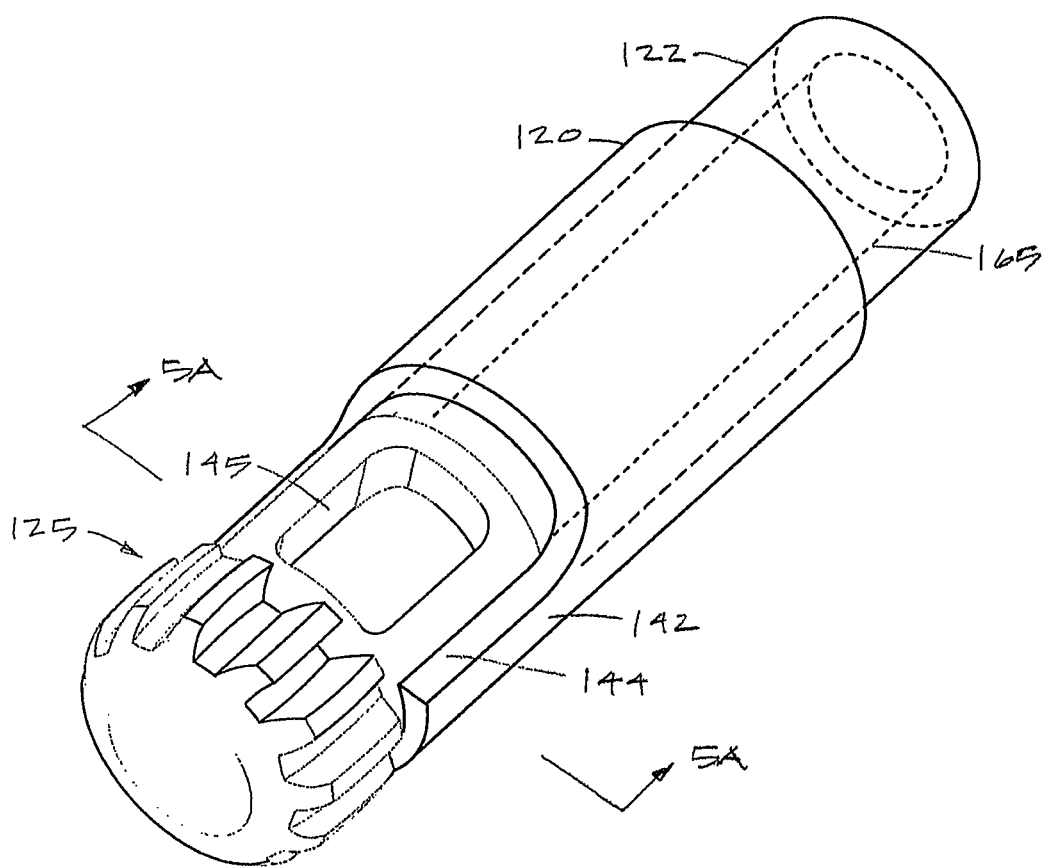
FIG. 2 is an enlarged perspective view of the ceramic cutting member of the arthroscopic cutter or burr assembly of FIG. 1.

In one variation shown in FIGS. 1-2, an arthroscopic cutter or burr assembly 100 is provided for cutting and removing hard tissue, which operates in a manner similar to commercially available metals shavers and burrs. FIG. 1 shows disposable burr assembly 100 that is adapted for detachable coupling to a handle 104 and motor drive unit 105 therein as shown in FIG. 3.

The cutter assembly 100 has a shaft 110 extending along longitudinal axis 115 that comprises an outer sleeve 120 and an inner sleeve 122 rotatably disposed therein with the inner sleeve 122 carrying a distal ceramic cutting member 125. The shaft 110 extends from a proximal hub assembly 128 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 3). The outer and inner sleeves 120 and 122 typically can be a thin wall stainless steel tube, but other materials can be used such as ceramics, metals, plastics or combinations thereof.

Referring to FIG. 2, the outer sleeve 120 extends to distal sleeve region 142 that has an open end and cut-out 144 that is adapted to expose a window 145 in the ceramic cutting member 125 during a portion of the inner sleeve's rotation. Referring to FIGS. 1 and 3, the proximal hub 128 of the burr assembly 100 is configured with a J-lock, snap-fit feature, screw thread or other suitable feature for detachably locking the hub assembly 128 into the handle 104. As can be seen in FIG. 1, the outer hub 140A includes a projecting key 146 that is adapted to mate with a receiving J-lock slot 148 in the handle 104 (see FIG. 3).

Figure 3:
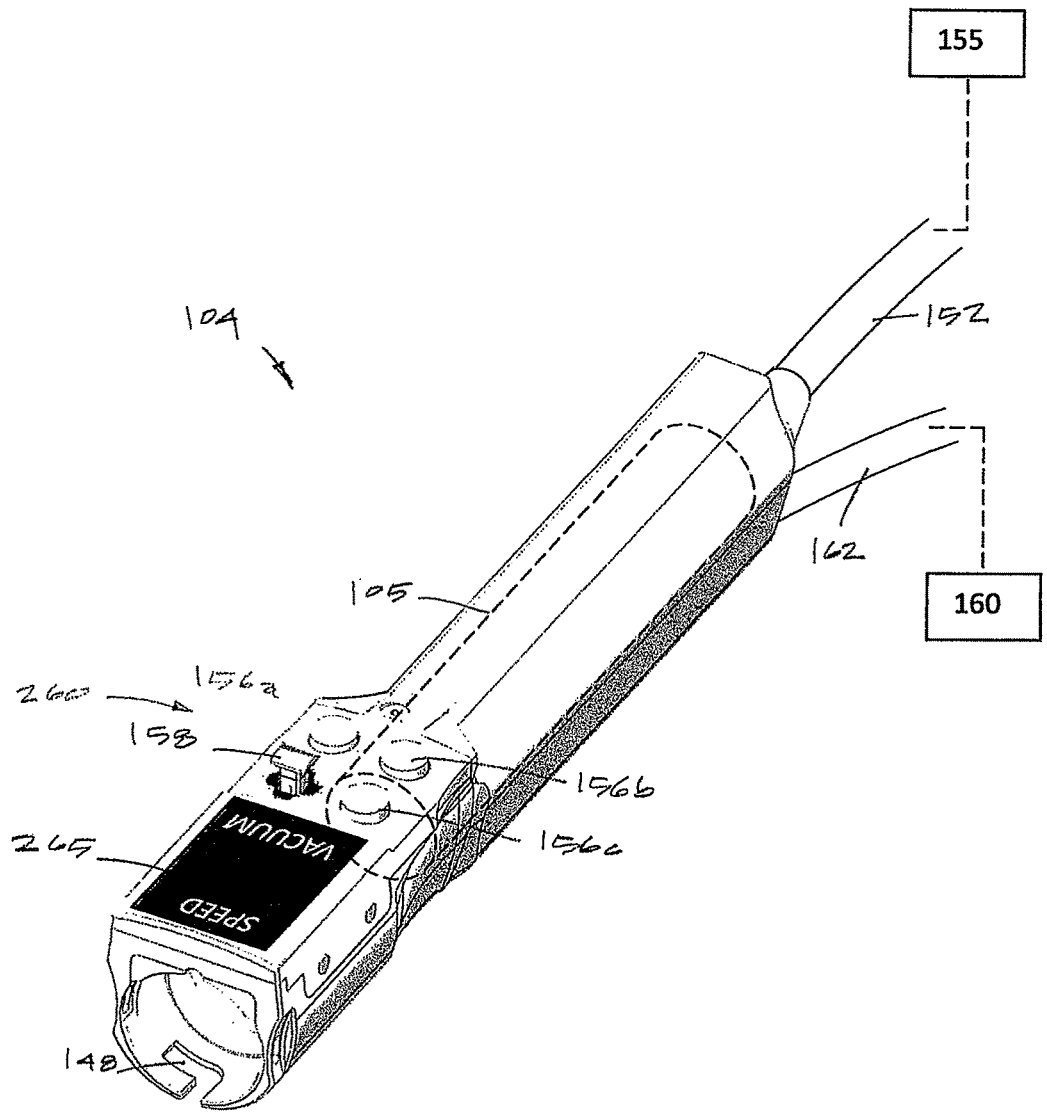
FIG. 3 is a perspective view of a handle body with a motor drive unit to which the burr assembly of FIG. 1 can be coupled, with the handle body including an LCD screen for displaying operating parameters of device during use together with a joystick and mode control actuators on the handle.

In FIG. 3, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 be moved forward and backward to adjust the rotational speed of the ceramic cutting member 125. The rotational speed of the cutter can continuously adjustable, or can be adjusted in increments up to 20,000 rpm. FIG. 3 further shows that negative pressure source 160 is coupled to aspiration tubing 162 which communicates with a flow channel in the handle 104 and lumen 165 in inner sleeve 122 which extends to window 145 in the ceramic cutting member 125 (FIG. 2).

Figure 4:
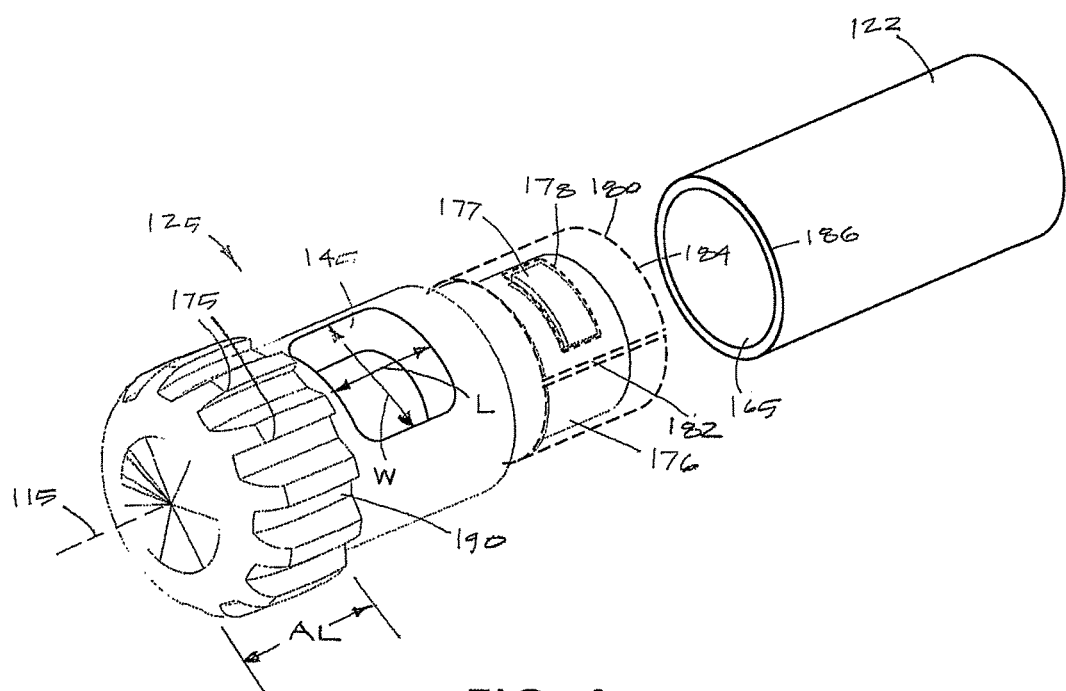
FIG. 4 is an enlarged perspective view of the ceramic cutting member showing a manner of coupling the cutter to a distal end of the inner sleeve of the burr assembly.

Now referring to FIGS. 2 and 4, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel provides ductile behavior which results in rapid cleaving and wear on sharp edges of a stainless steel cutting member. In contrast, technical ceramic materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

CHART A

|  | Hardness (GPa) | Fracture Toughness ($MPam^{1/2}$) | Ratio Hardness to Fracture Toughness |
|---|---|---|---|
| Cortical bone | 0.8 | 12 | .07:1 |
| Stainless steel 304 | 2.1 | 228 | .01:1 |
| Yttria-stabilized zirconia (YTZP) |  |  |  |
| YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) |  |  |  |
| Dura-Z ® (Superior Technical Ceramics) | 12.0 | 11 | 1.09:1 |
| MSZ 200 (CoorsTek) | 11.7 | 12 | 0.98:1 |
| Zirconia toughened alumina (ZTA) |  |  |  |
| YTA-14 (Superior Technical Ceramics) | 14.0 | 5 | 2.80:1 |
| ZTA (CoorsTek) | 14.8 | 6 | 2.47:1 |
| Ceria stabilized zirconia |  |  |  |
| CSZ (Superior Technical Ceramics) | 11.7 | 12 | 0.98:1 |
| Silicon Nitride |  |  |  |
| SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics— Electric and Magnetic Ceramics, Bioceramics, Ceramics and Environment* (2011).

In one variation, the ceramic cutting member 125 is fabricated of an yttria-stabilized zirconia as is known in the field of technical ceramics, and can be provided by CoorsTek Inc., 16000 Table Mountain Pkwy., Golden, Colo. 80403 or Superior Technical Ceramics Corp., 600 Industrial Park Rd., St. Albans City, Vt. 05478. Other technical ceramics that may be used consist of magnesia-stabilized zirconia, ceria-stabilized zirconia, zirconia toughened alumina and silicon nitride. In general, in one aspect of the invention, the monolithic ceramic cutting member 125 has a hardness rating of at least 8 Gpa (kg/mm$^2$). In another aspect of the invention, the ceramic cutting member 125 has a fracture toughness of at least 2 MPam$^{1/2}$.

The fabrication of such ceramics or monoblock components are known in the art of technical ceramics, but have not been used in the field of arthroscopic or endoscopic cutting or resecting devices. Ceramic part fabrication includes molding, sintering and then heating the molded part at high temperatures over precise time intervals to transform a compressed ceramic powder into a ceramic monoblock which can provide the hardness range and fracture toughness range as described above. In one variation, the molded ceramic member part can have additional strengthening through hot isostatic pressing of the part. Following the ceramic fabrication process, a subsequent grinding process optionally may be used to sharpen the cutting edges 175 of the burr (see FIGS. 2 and 4).

In FIG. 4, it can be seen that in one variation, the proximal shaft portion 176 of cutting member 125 includes projecting elements 177 which are engaged by receiving openings 178 in a stainless steel split collar 180 shown in phantom view. The split collar 180 can be attached around the shaft portion 176 and projecting elements 177 and then laser welded along weld line 182. Thereafter, proximal end 184 of collar 180 can be laser welded to the distal end 186 of stainless steel inner sleeve 122 to mechanically couple the ceramic body 125 to the metal inner sleeve 122. In another aspect of the invention, the ceramic material is selected to have a coefficient of thermal expansion between is less than 10 (1×10$^6$/° C.) which can be close enough to the coefficient of thermal expansion of the metal sleeve 122 so that thermal stresses will be reduced in the mechanical coupling of the ceramic member 125 and sleeve 122 as just described. In another variation, a ceramic cutting member can be coupled to metal sleeve 122 by brazing, adhesives, threads or a combination thereof.

Referring to FIGS. 1 and 4, the ceramic cutting member 125 has window 145 therein which can extend over a radial angle of about 10° to 90° of the cutting member's shaft. In the variation of FIG. 1, the window is positioned proximally to the cutting edges 175, but in other variations, one or more windows or openings can be provided and such openings can extend in the flutes 190 (see FIG. 6) intermediate the cutting edges 175 or around a rounded distal nose of the ceramic cutting member 125. The length L of window 145 can range from 2 mm to 10 mm depending on the diameter and design of the ceramic member 125, with a width W of 1 mm to 10 mm.

Figure 6:
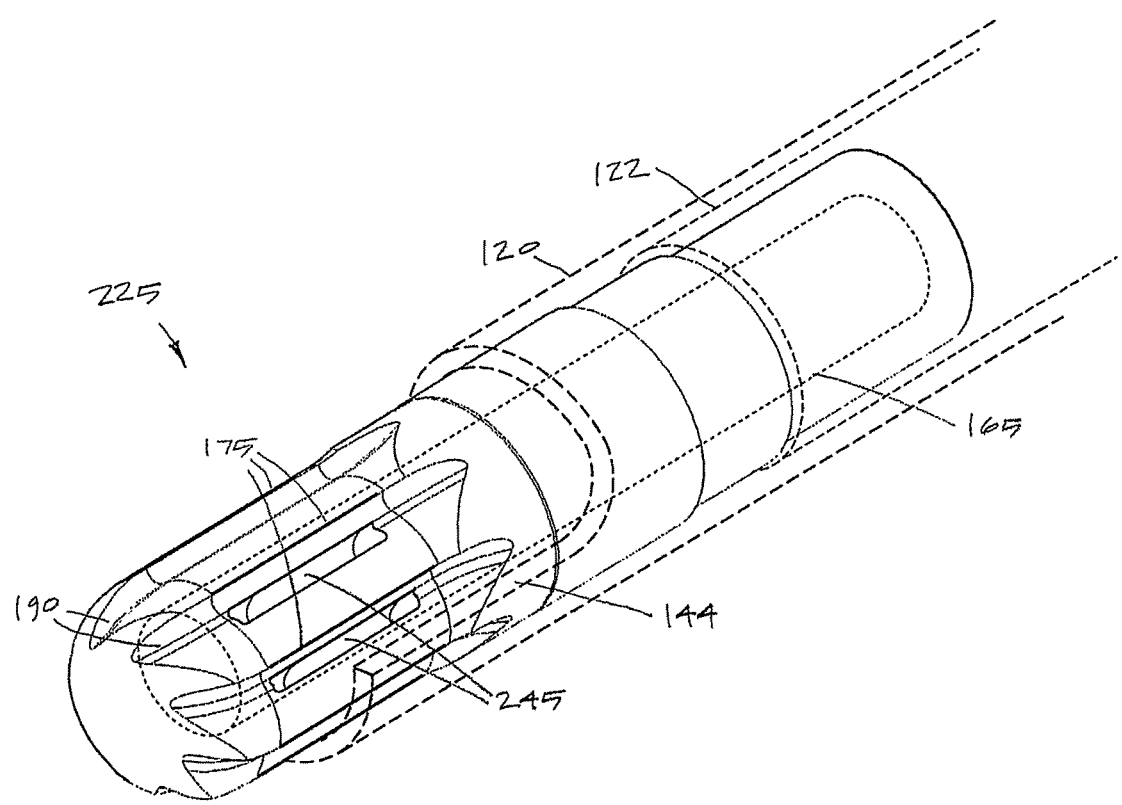
FIG. 6 is a perspective view of another ceramic cutting member carried at the distal end of an inner sleeve with a somewhat rounded distal nose and deeper flutes than the cutting member of FIGS. 2 and 4, and with aspiration openings or ports formed in the flutes.
Figure 7:
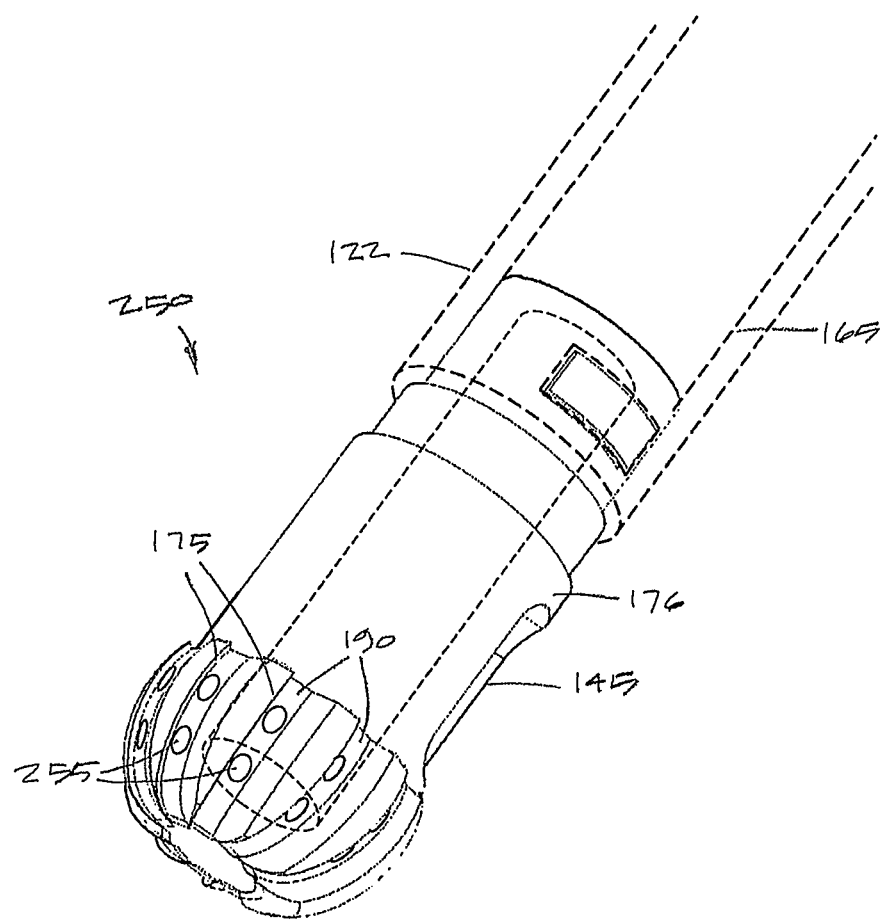
FIG. 7 is a perspective view of another ceramic cutting member with cutting edges that extend around a distal nose of the cutter together with an aspiration window in the shaft portion and aspiration openings in the flutes.

FIGS. 1 and 4 shows the ceramic burr or cutting member 125 with a plurality of sharp cutting edges 175 which can extend helically, axially, longitudinally or in a cross-hatched configuration around the cutting member, or any combination thereof. The number of cutting edges 175 ands intermediate flutes 190 can range from 2 to 100 with a flute depth ranging from 0.10 mm to 2.5 mm. In the variation shown in FIGS. 2 and 4, the outer surface or periphery of the cutting edges 175 is cylindrical, but such a surface or periphery can be angled relative to axis 115 or rounded as shown in FIGS. 6 and 7. The axial length AL of the cutting edges can range between 1 mm and 10 mm. While the cutting edges 175 as depicted in FIG. 4 are configured for optimal bone cutting or abrading in a single direction of rotation, it should be appreciated the that the controller 155 and motor drive 105 can be adapted to rotate the ceramic cutting member 125 in either rotational direction, or oscillate the cutting member back and forth in opposing rotational directions.

Figure 5A:
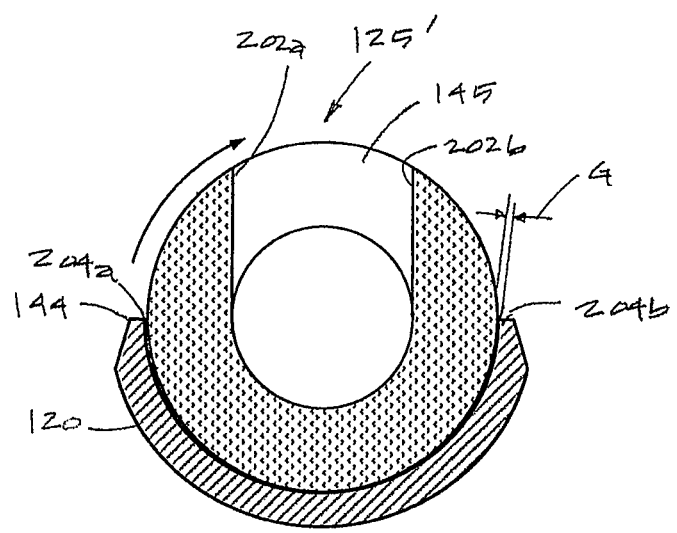
FIG. 5A is a cross-sectional view of a cutting assembly similar to that of FIG. 2 taken along line 5A-5A showing the close tolerance between sharp cutting edges of a window in a ceramic cutting member and sharp lateral edges of the outer sleeve which provides a scissor-like cutting effect in soft tissue.
Figure 5B:
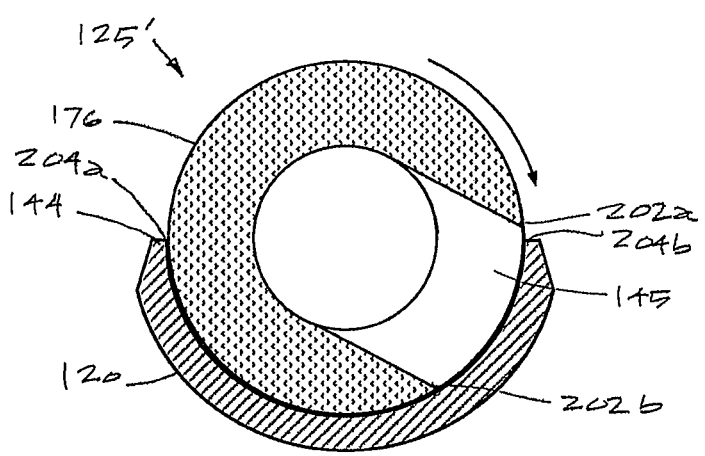
FIG. 5B is a cross-sectional view of the cutting assembly of FIG. 5A with the ceramic cutting member in a different rotational position than in FIG. 5A.

FIGS. 5A-5B illustrate a sectional view of the window 145 and shaft portion 176 of a ceramic cutting member 125' that is very similar to the ceramic member 125 of FIGS. 2 and 4. In this variation, the ceramic cutting member has window 145 with one or both lateral sides configured with sharp cutting edges 202a and 202b which are adapted to resect tissue when rotated or oscillated within close proximity, or in scissor-like contact with, the lateral edges 204a and 204b of the sleeve walls in the cut-out portion 144 of the distal end of outer sleeve 120 (see FIG. 2). Thus, in general, the sharp edges of window 145 can function as a cutter or shaver for resecting soft tissue rather than hard tissue or bone. In this variation, there is effectively no open gap G between the sharp edges 202a and 202b of the ceramic cutting member 125' and the sharp lateral edges 204a, 204b of the sleeve 120. In another variation, the gap G between the window cutting edges 202a, 202b and the sleeve edges 204a, 204b is less than about 0.020 inch, or less than 0.010 inch.

FIG. 6 illustrates another variation of ceramic cutting member 225 coupled to an inner sleeve 122 in phantom view. The ceramic cutting member again has a plurality of sharp cutting edges 175 and flutes 190 therebetween. The outer sleeve 120 and its distal opening and cut-out shape 144 are also shown in phantom view. In this variation, a plurality of windows or opening 245 are formed within the flutes 190 and communicate with the interior aspiration channel 165 in the ceramic member as described previously.

FIG. 7 illustrates another variation of ceramic cutting member 250 coupled to an inner sleeve 122 (phantom view) with the outer sleeve not shown. The ceramic cutting member 250 is very similar to the ceramic cutter 125 of FIGS. 1, 2 and 4, and again has a plurality of sharp cutting edges 175 and flutes 190 therebetween. In this variation, a plurality of windows or opening 255 are formed in the flutes 190 intermediate the cutting edges 175 and another window 145 is provided in a shaft portion 176 of ceramic member 225 as described previously. The openings 255 and window 145 communicate with the interior aspiration channel 165 in the ceramic member as described above.

It can be understood that the ceramic cutting members can eliminate the possibility of leaving metal particles in a treatment site. In one aspect of the invention, a method of preventing foreign particle induced inflammation in a bone treatment site comprises providing a rotatable cutter fabricated of a ceramic material having a hardness of at least 8 Gpa (kg/mm$^2$) and/or a fracture toughness of at least 2 MPam$^{1/2}$ and rotating the cutter to cut bone without leaving any foreign particles in the treatment site. The method includes removing the cut bone tissue from the treatment site through an aspiration channel in a cutting assembly.

Figure 8:
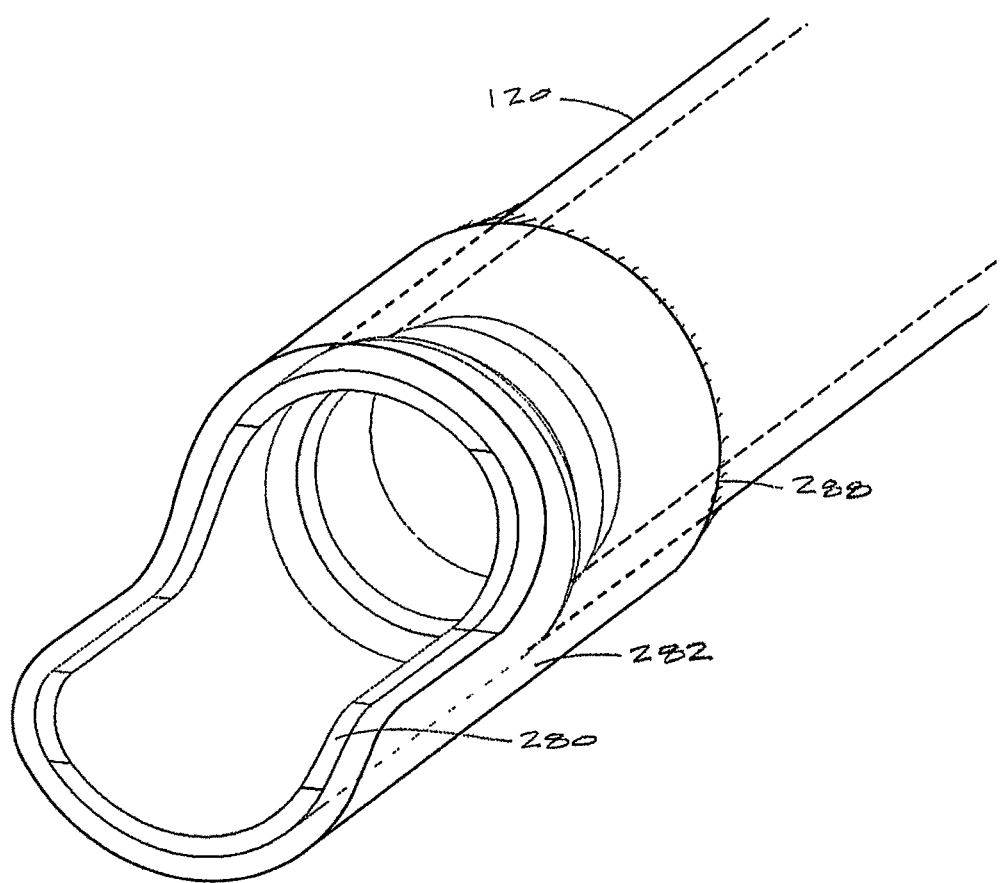
FIG. 8 is a perspective view of a ceramic housing carried at the distal end of the outer sleeve.

FIG. 8 illustrates variation of an outer sleeve assembly with the rotating ceramic cutter and inner sleeve not shown. In the previous variations, such as in FIGS. 1, 2 and 6, shaft portion 176 of the ceramic cutter 125 rotates in a metal outer sleeve 120. FIG. 8 illustrates another variation in which a ceramic cutter (not shown) would rotate in a ceramic housing 280. In this variation, the shaft or a ceramic cutter would thus rotate is a similar ceramic body which may be advantageous when operating a ceramic cutter at high rotational speeds. As can be seen in FIG. 8, a metal distal metal housing 282 is welded to the outer sleeve 120 along weld line 288. The distal metal housing 282 is shaped to support and provide strength to the inner ceramic housing 282.

Figure 9:
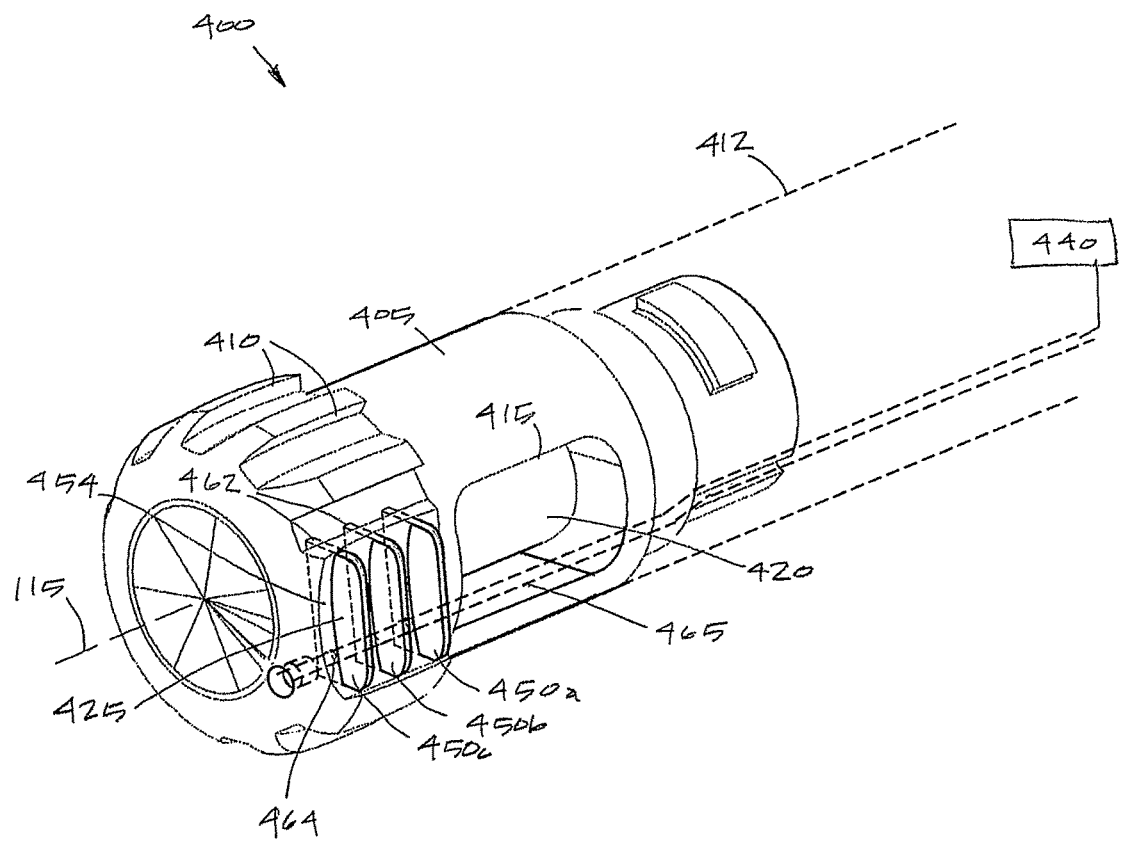
FIG. 9 is a perspective of another variation of a ceramic member with cutting edges that includes an aspiration window and an electrode arrangement positioned distal to the window.
Figure 10:
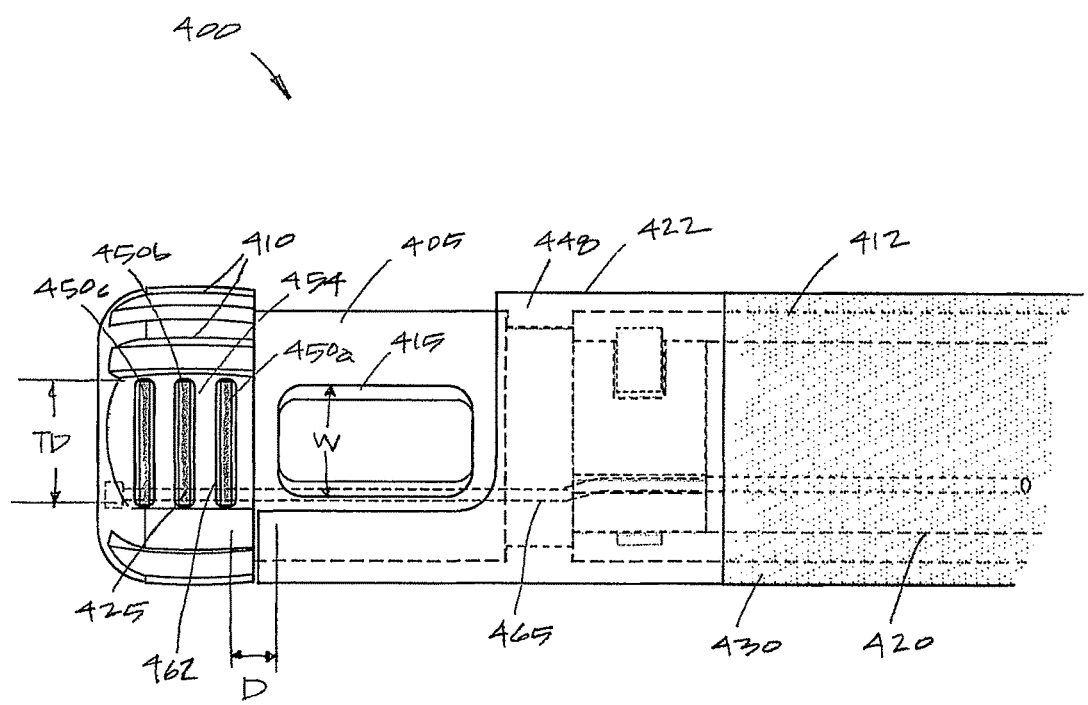
FIG. 10 is an elevational view of a ceramic member and shaft of FIG. 9 showing the width and position of the electrode arrangement in relation to the window.
Figure 11:
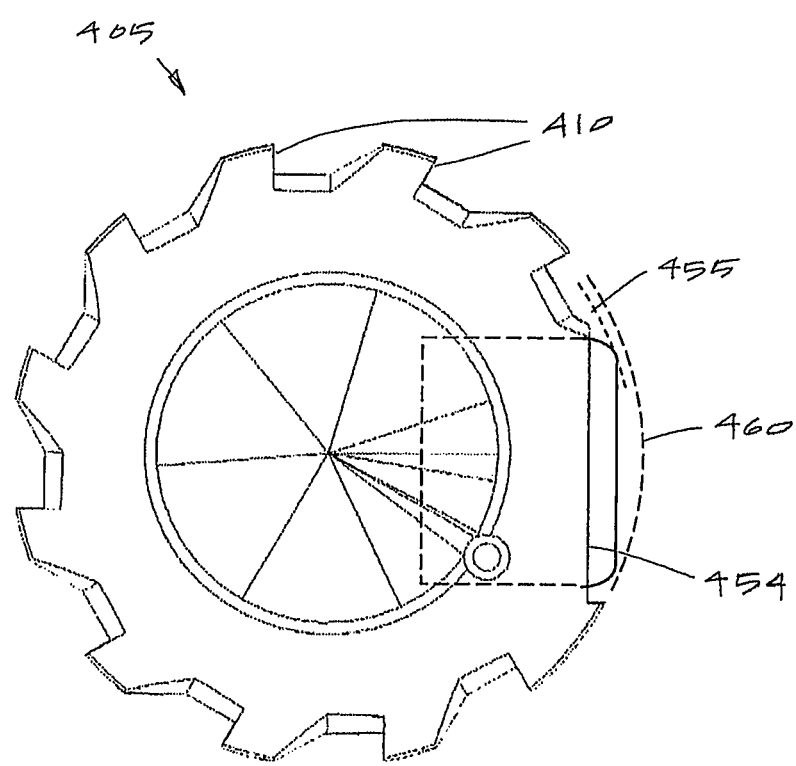
FIG. 11 is an end view of a ceramic member of FIGS. 9-10 the outward periphery of the electrode arrangement in relation to the rotational periphery of the cutting edges of the ceramic member.

FIGS. 9-11 are views of an alternative tissue resecting assembly or working end 400 that includes a ceramic member 405 with cutting edges 410 in a form similar to that described previously. FIG. 9 illustrates the monolithic ceramic member 405 carried as a distal tip of a shaft or inner sleeve 412 as described in previous embodiments. The ceramic member 405 again has a window 415 that communicates with aspiration channel 420 in shaft 412 that is connected to negative pressure source 160 as described previously. The inner sleeve 412 is operatively coupled to a motor drive 105 and rotates in an outer sleeve 422 of the type shown in FIG. 2. The outer sleeve 422 is shown in FIG. 10.

In the variation illustrated in FIG. 9, the ceramic member 405 carries an electrode arrangement 425, or active electrode, having a single polarity that is operatively connected to an RF source 440. A return electrode, or second polarity electrode 430, is provided on the outer sleeve 422 as shown in FIG. 10. In one variation, the outer sleeve 422 can comprise an electrically conductive material such as stainless steel to thereby function as return electrode 445, with a distal portion of outer sleeve 422 is optionally covered by a thin insulating layer 448 such as parylene, to space apart the active electrode 425 from the return electrode 430.

The active electrode arrangement 425 can consist of a single conductive metal element or a plurality of metal elements as shown in FIGS. 9 and 10. In one variation shown in FIG. 9, the plurality of electrode elements 450a, 450b and 450c extend transverse to the longitudinal axis 115 of ceramic member 405 and inner sleeve 412 and are slightly spaced apart in the ceramic member. In one variation shown in FIGS. 9 and 10, the active electrode 425 is spaced distance D from the distal edge 452 of window 415 which is less than 5 mm and often less than 2 mm for reasons described below. The width W and length L of window 415 can be the same as described in a previous embodiment with reference to FIG. 4.

As can be seen in FIGS. 9 and 11, the electrode arrangement 425 is carried intermediate the cutting edges 410 of the ceramic member 405 in a flattened region 454 where the cutting edges 410 have been removed. As can be best understood from FIG. 11, the outer periphery 455 of active electrode 425 is within the cylindrical or rotational periphery of the cutting edges 410 when they rotate. In FIG. 11, the rotational periphery of the cutting edges is indicated at 460. The purpose of the electrode's outer periphery 455 being equal to, or inward from, the cutting edge periphery 460 during rotation is to allow the cutting edges 410 to rotate at high RPMs to engage and cut bone or other hard tissue without the surface or the electrode 425 contacting the targeted tissue.

FIG. 9 further illustrates a method of fabricating the ceramic member 405 with the electrode arrangement 425 carried therein. The molded ceramic member 405 is fabricated with slots 462 that receive the electrode elements 450a-450c, with the electrode elements fabricated from stainless steel, tungsten or a similar conductive material. Each electrode element 450a-450c has a bore 464 extending therethrough for receiving an elongated wire electrode element 465. As can be seen in FIG. 9, and the elongated wire electrode 465 can be inserted from the distal end of the ceramic member 405 through a channel in the ceramic member 405 and through the bores 464 in the electrode elements 450a-450c. The wire electrode 465 can extend through the shaft 412 and is coupled to the RF source 440. The wire electrode element 465 thus can be used as a means of mechanically locking the electrode elements 450a-450c in slots 462 and also as a means to deliver RF energy to the electrode 425.

Another aspect of the invention is illustrated in FIGS. 9-10 wherein it can be seen that the electrode arrangement 425 has a transverse dimension TD relative to axis 115 that is substantial in comparison to the window width W as depicted in FIG. 10. In one variation, the electrode's transverse dimension TD is at least 50% of the window width W, or the transverse dimension TD is at least 80% of the window width W. In the variation of FIGS. 9-10, the electrode transverse dimension TD is 100% or more of the window width W. It has been found that tissue debris and byproducts from RF ablation are better captured and extracted by a window 415 that is wide when compared to the width of the RF plasma ablation being performed.

In general, the tissue resecting system comprises an elongated shaft with a distal tip comprising a ceramic member, a window in the ceramic member connected to an interior channel in the shaft and an electrode arrangement in the ceramic member positioned distal to the window and having a width that is at 50% of the width of the window, at 80% of the width of the window or at 100% of the width of the window. Further, the system includes a negative pressure source 160 in communication with the interior channel 420.

Figure 12A:
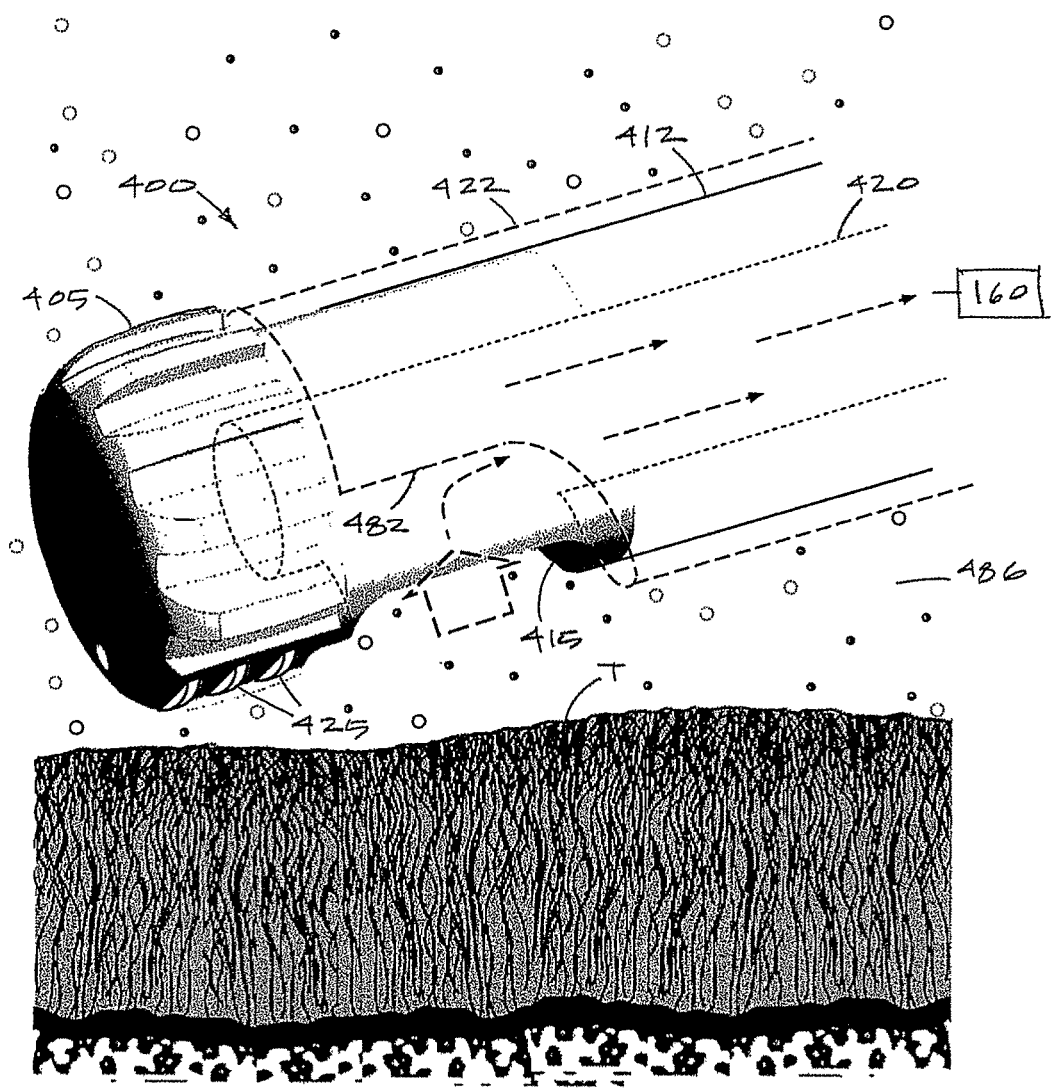
FIG. 12A is a schematic view of the working end and ceramic cutting member of FIGS. 9-11 illustrating a step in a method of use.
Figure 12B:
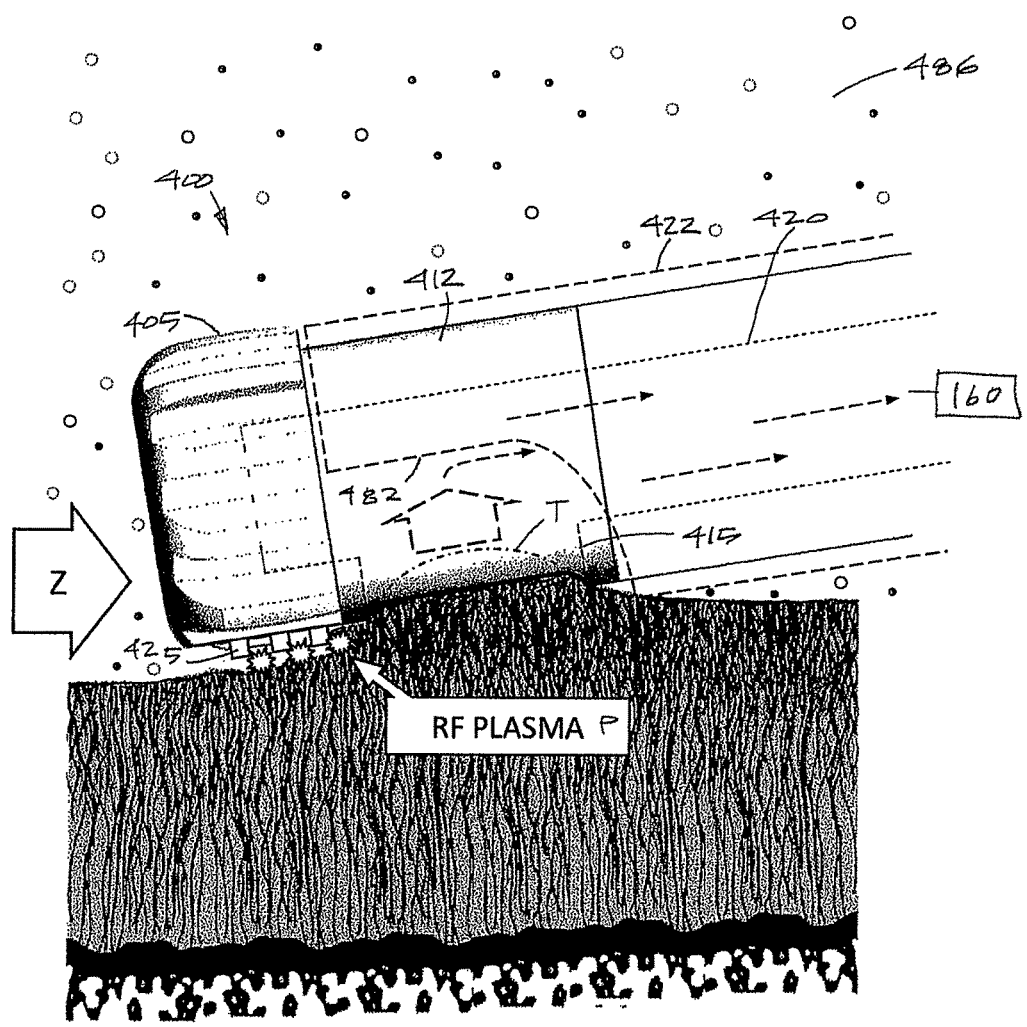
FIG. 12B is another view of the working end of FIG. 12A illustrating a subsequent step in a method of use to ablate a tissue surface.
Figure 12C:
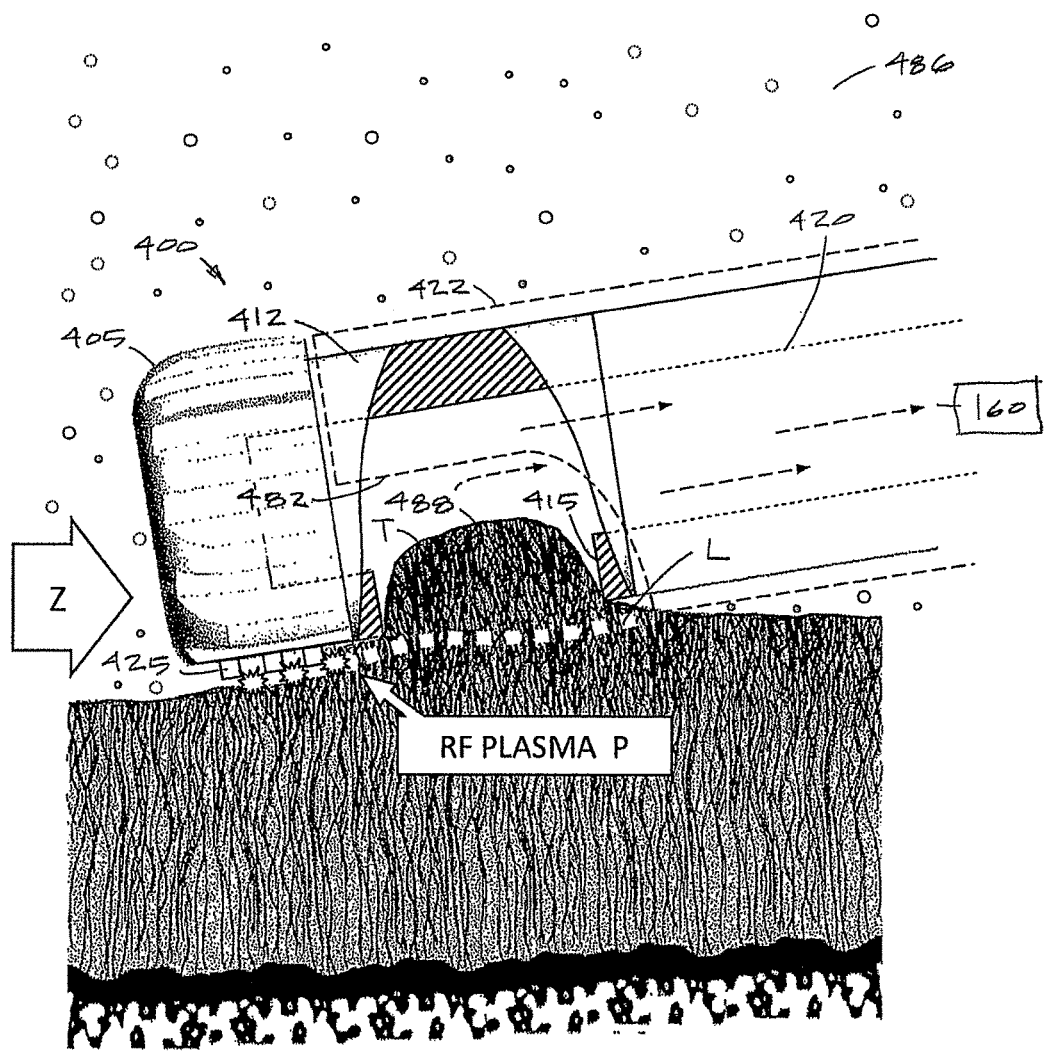
FIG. 12C is a view of the working end of FIG. 12A illustrating a method of tissue resection and aspiration of tissue chips to rapidly remove volumes of tissue.

Now turning to FIGS. 12A-12C, a method of use of the resecting assembly 400 of FIG. 9 can be explained. In FIG. 12A, the system and a controller is operated to stop rotation of the ceramic member 405 in a selected position were the window 415 is exposed in the cut-out 482 of the open end of outer sleeve 422 shown in phantom view. In one variation, a controller algorithm can be adapted to stop the rotation of the ceramic 405 that uses a Hall sensor 484a in the handle 104 (see FIG. 3) that senses the rotation of a magnet 484b carried by inner sleeve hub 140B as shown in FIG. 2. The controller algorithm can receive signals from the Hall sensor which indicated the rotational position of the inner sleeve 412 and ceramic member relative to the outer sleeve 422. The magnet 484b can be positioned in the hub 140B (FIG. 2) so that when sensed by the Hall sensor, the controller algorithm can de-activate the motor drive 105 so as to stop the rotation of the inner sleeve in the selected position.

Under endoscopic vision, referring to FIG. 12B, the physician then can position the electrode arrangement 425 in contact with tissue targeted T for ablation and removal in a working space filled with fluid 486, such as a saline solution which enables RF plasma creation about the electrode. The negative pressure source 160 is activated prior to or contemporaneously with the step of delivering RF energy to electrode 425. Still referring to FIG. 12B, when the ceramic member 405 is positioned in contact with tissue and translated in the direction of arrow Z, the negative pressure source 160 suctions the targeted tissue into the window 415. At the same time, RF energy delivered to electrode arrangement 425 creates a plasma P as is known in the art to thereby ablate tissue. The ablation then will be very close to the window 415 so that tissue debris, fragments, detritus and byproducts will be aspirated along with fluid 486 through the window 415 and outwardly through the interior extraction channel 420 to a collection reservoir. In one method shown schematically in FIG. 12B, a light movement or translation of electrode arrangement 425 over the targeted tissue will ablate a surface layer of the tissue and aspirate away the tissue detritus.

FIG. 12C schematically illustrates a variation of a method which is of particular interest. It has been found if suitable downward pressure on the working end 400 is provided, then axial translation of working end 400 in the direction arrow Z in FIG. 12C, together with suitable negative pressure and the RF energy delivery will cause the plasma P to undercut the targeted tissue along line L that is suctioned into window 415 and then cut and scoop out a tissue chips indicated at 488. In effect, the working end 400 then can function more as a high volume tissue resecting device instead of, or in addition to, its ability to function as a surface ablation tool. In this method, the cutting or scooping of such tissue chips 488 would allow the chips to be entrained in outflows of fluid 486 and aspirated through the extraction channel 420. It has been found that this system with an outer shaft diameter of 7.5 mm, can perform a method of the invention can ablate, resect and remove tissue greater than 15 grams/min, greater than 20 grams/min, and greater than 25 grams/min.

In general, a method corresponding to the invention includes providing an elongated shaft with a working end 400 comprising an active electrode 425 carried adjacent to a window 415 that opens to an interior channel in the shaft which is connected to a negative pressure source, positioning the active electrode and window in contact with targeted tissue in a fluid-filled space, activating the negative pressure source to thereby suction targeted tissue into the window and delivering RF energy to the active electrode to ablate tissue while translating the working end across the targeted tissue. The method further comprises aspirating tissue debris through the interior channel 420. In a method, the working end 400 is translated to remove a surface portion of the targeted tissue. In a variation of the method, the working end 400 is translated to undercut the targeted tissue to thereby remove chips 488 of tissue.

Figure 13A:
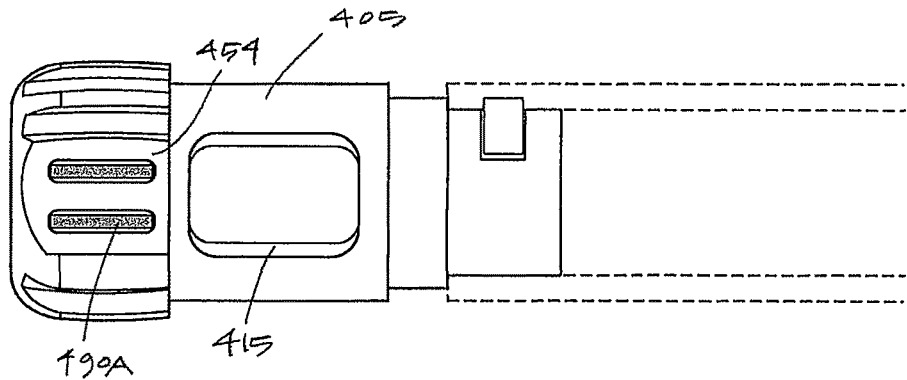
FIG. 13A is an elevational view of an alternative ceramic member and shaft similar to that of FIG. 9 illustrating an electrode variation.
Figure 13B:
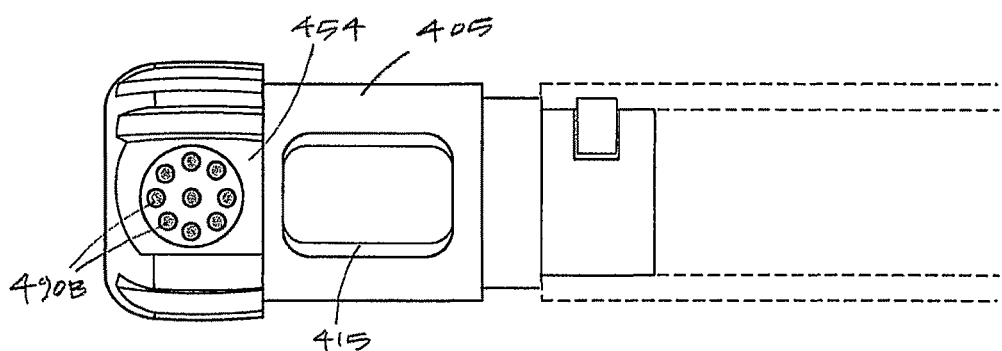
FIG. 13B is an elevational view of another ceramic member similar to that of FIG. 12A illustrating another electrode variation.
Figure 13C:
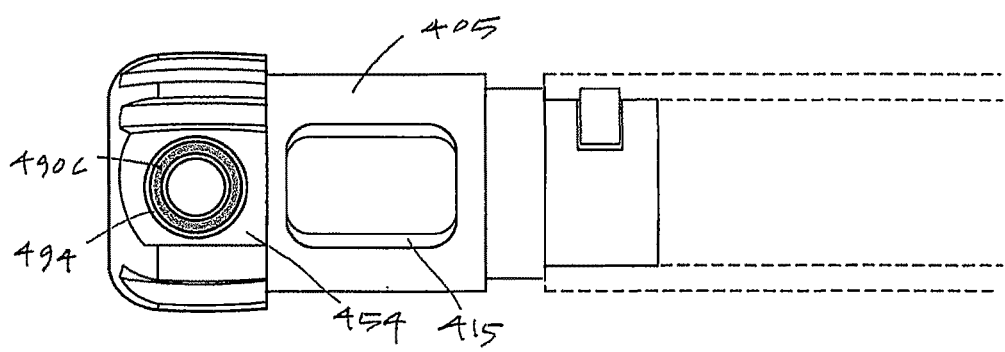
FIG. 13C is an elevational view of another ceramic member similar to that of FIGS. 12A-12B illustrating another electrode variation.

Now turning to FIGS. 13A-13C, other distal ceramic tips of cutting assemblies are illustrated that are similar to that of FIGS. 9-11, except the electrode configurations carried by the ceramic members 405 are varied. In FIG. 13A, the electrode 490A comprises one or more electrode elements extending generally axially distally from the window 415. FIG. 13B illustrates an electrode 490B that comprises a plurality of wire-like elements 492 projecting outwardly from surface 454. FIG. 13C shows electrode 490C that comprises a ring-like element that is partly recessed in a groove 494 in the ceramic body. All of these variations can produce an RF plasma that is effective for surface ablation of tissue, and are positioned adjacent to window 415 to allow aspiration of tissue detritus from the site.

Figure 14:
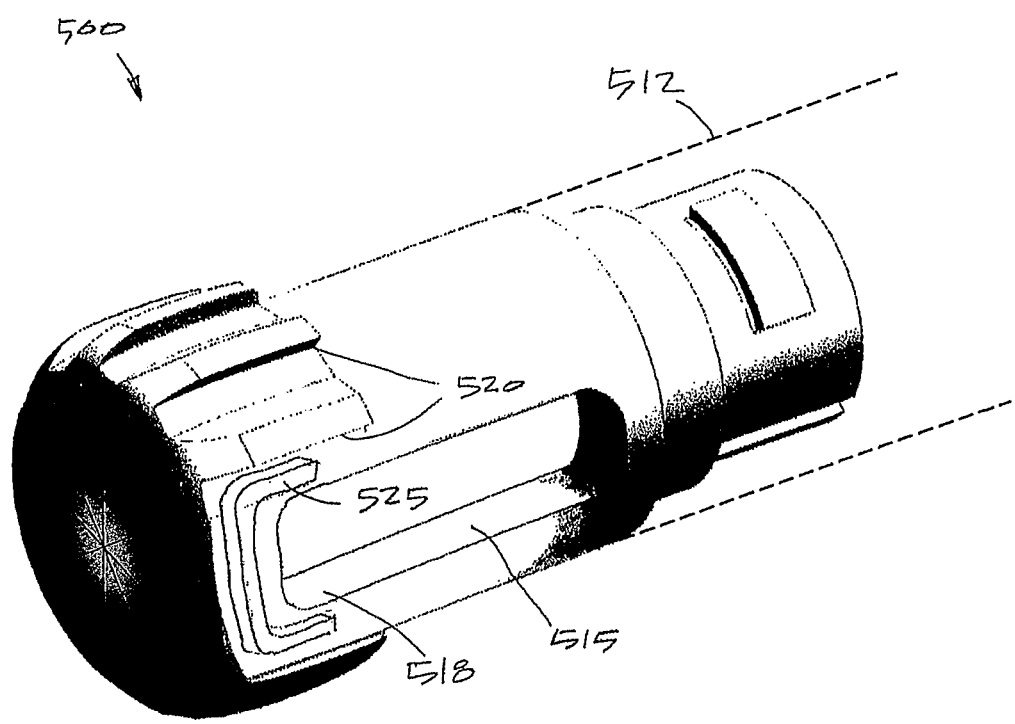
FIG. 14 is a perspective view of an alternative working end and ceramic cutting member with an electrode partly encircling a distal portion of an aspiration window.

FIG. 14 illustrates another variation of a distal ceramic tip 500 of an inner sleeve 512 that is similar to that of FIG. 9 except that the window 515 has a distal portion 518 that extends distally between the cutting edges 520, which is useful for aspirating tissue debris cut by high speed rotation of the cutting edges 520. Further, in the variation of FIG. 14, the electrode 525 encircles a distal portion 518 of window 515 which may be useful for removing tissue debris that is ablated by the electrode when the ceramic tip 500 is not rotated but translated over the targeted tissue as described above in relation to FIG. 12B. In another variation, a distal tip 500 as shown in FIG. 14 can be energized for RF ablation at the same time that the motor drive rotates back and forth (or oscillates) the ceramic member 500 in a radial arc ranging from 1° to 180° and more often from 10° to 90°.

Figure 15A:
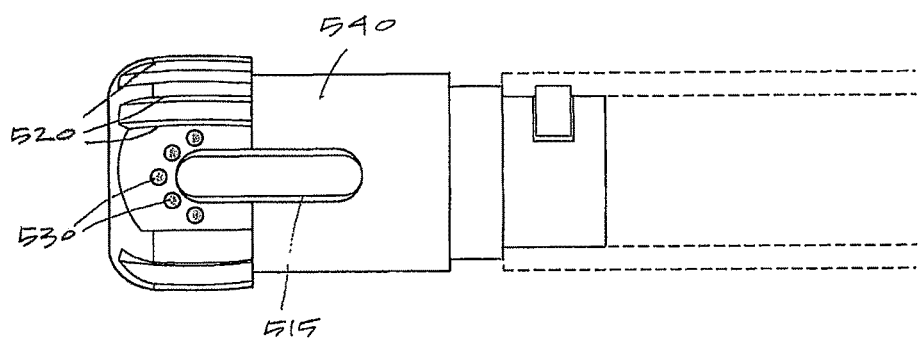
FIG. 15A is an elevational view of a working end variation with an electrode arrangement partly encircling a distal end of the aspiration window.
Figure 15B:
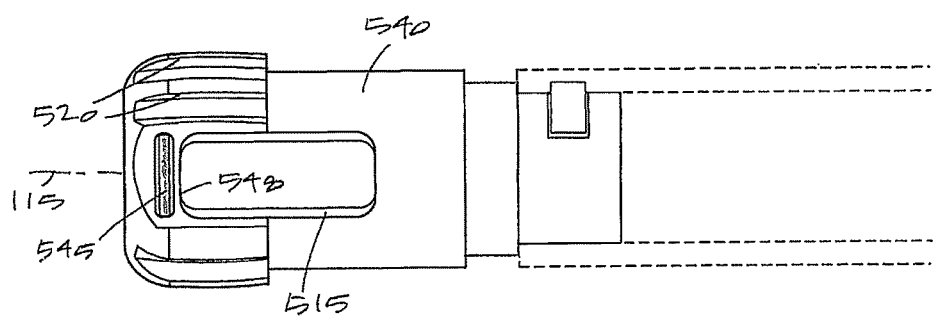
FIG. 15B is an elevational view of another working end variation with an electrode positioned adjacent a distal end of the aspiration window.

FIGS. 15A-15B illustrate other distal ceramic tips 540 and 540' that are similar to that of FIG. 14 except the electrode configurations differ. In FIG. 15A, the window 515 has a distal portion 518 that again extends distally between the cutting edges 520, with electrode 530 comprising a plurality of projecting electrode elements that extend partly around the window 515. FIG. 15B shows a ceramic tip 540' with window 515 having a distal portion 518 that again extends distally between the cutting edges 520. In this variation, the electrode 545 comprises a single blade element that extends transverse to axis 115 and is in close proximity to the distal end 548 of window 515.

Figure 16:
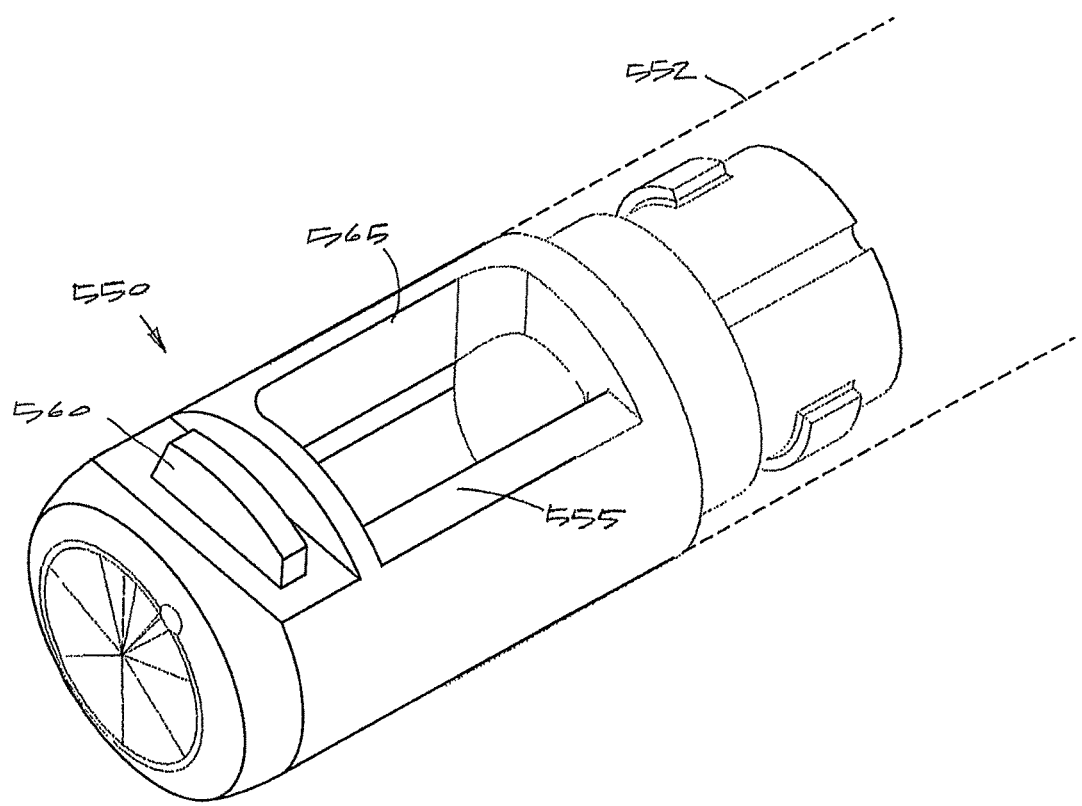
FIG. 16 is a perspective view of a variation of a working end and ceramic member with an electrode adjacent a distal end of an aspiration window having a sharp lateral edge for cutting tissue.

FIG. 16 illustrates another variation of distal ceramic tip 550 of an inner sleeve 552 that is configured without the sharp cutting edges 410 of the embodiment of FIGS. 9-11. In other respects, the arrangement of the window 555 and the electrode 560 is the same as described previously. Further, the outer periphery of the electrode is similar to the outward surface of the ceramic tip 550. In the variation of FIG. 16, the window 555 has at least one sharp edge 565 for cutting soft tissue when the assembly is rotated at a suitable speed from 500 to 5,000 rpm. When the ceramic tip member 550 is maintained in a stationary position and translated over targeted tissue, the electrode 560 can be used to ablate surface layers of tissue as described above.

Figure 17:
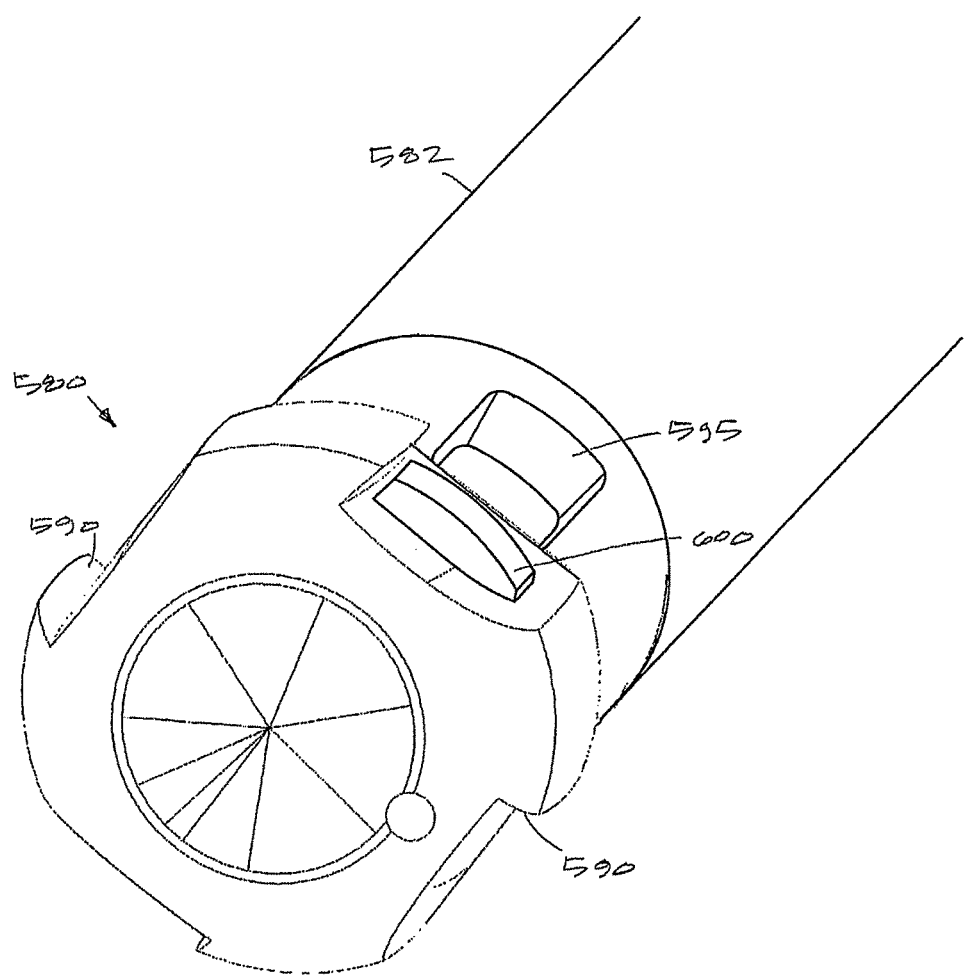
FIG. 17 is a perspective view of a variation of a working end and ceramic member with four cutting edges and an electrode adjacent a distal end of an aspiration window.

FIG. 17 depicts another variation of distal ceramic tip 580 coupled to an inner sleeve 582 that again has sharp burr edges or cutting edges 590 as in the embodiment of FIGS. 9-11. In this variation, the ceramic monolith has only 4 sharp edges 590 which has been found to work well for cutting bone at high RPMs, for example from 8,000 RPM to 20,000 RPM. In this variation, the arrangement of window 595 and electrode 600 is the same as described previously. Again, the outer periphery of electrode 595 is similar to the outward surface of the cutting edges 590.

Figure 18:
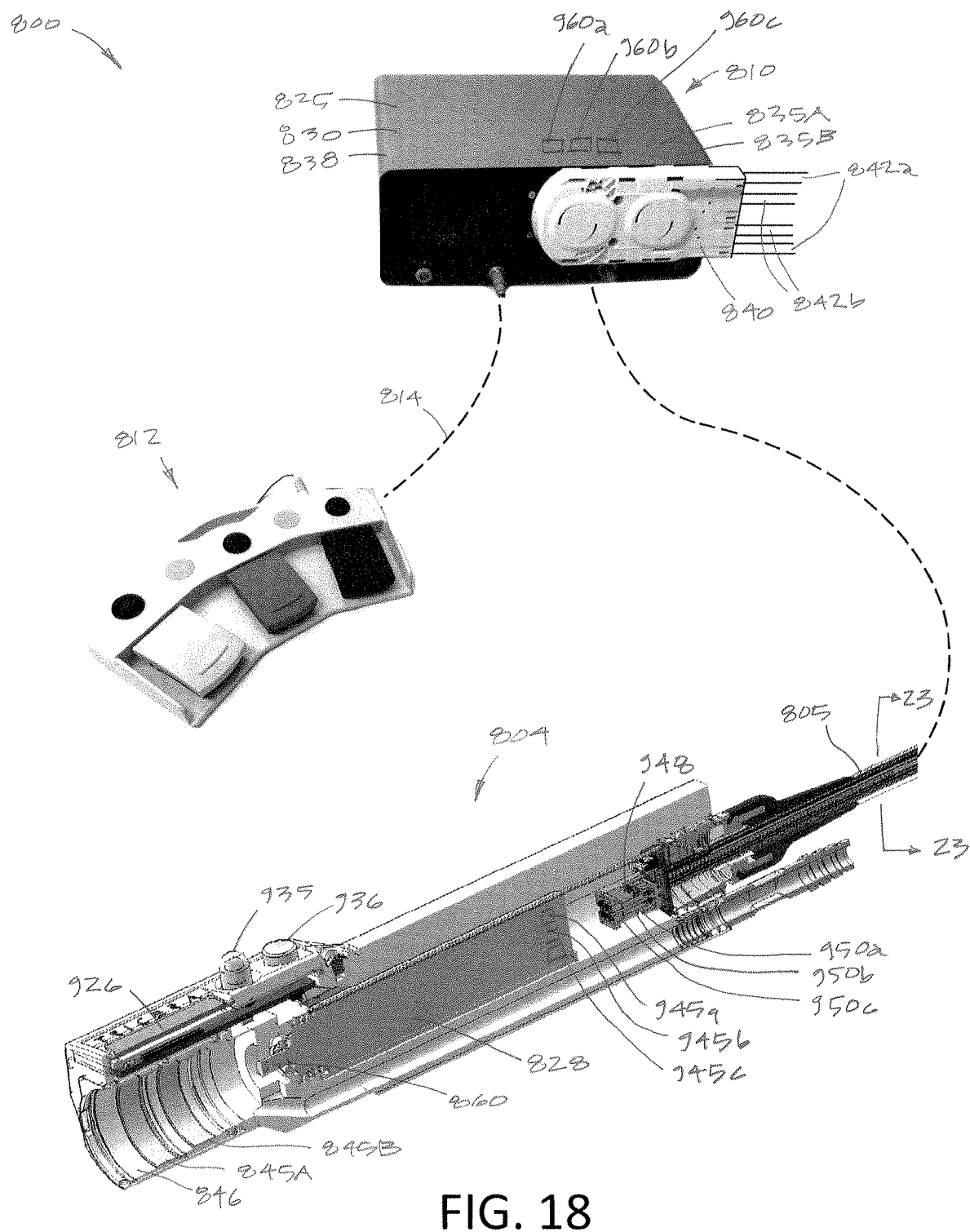
FIG. 18 is perspective view of an arthroscopic system including a control and power console, a footswitch and a re-usable motor carrying a motor drive unit.
Figure 19:
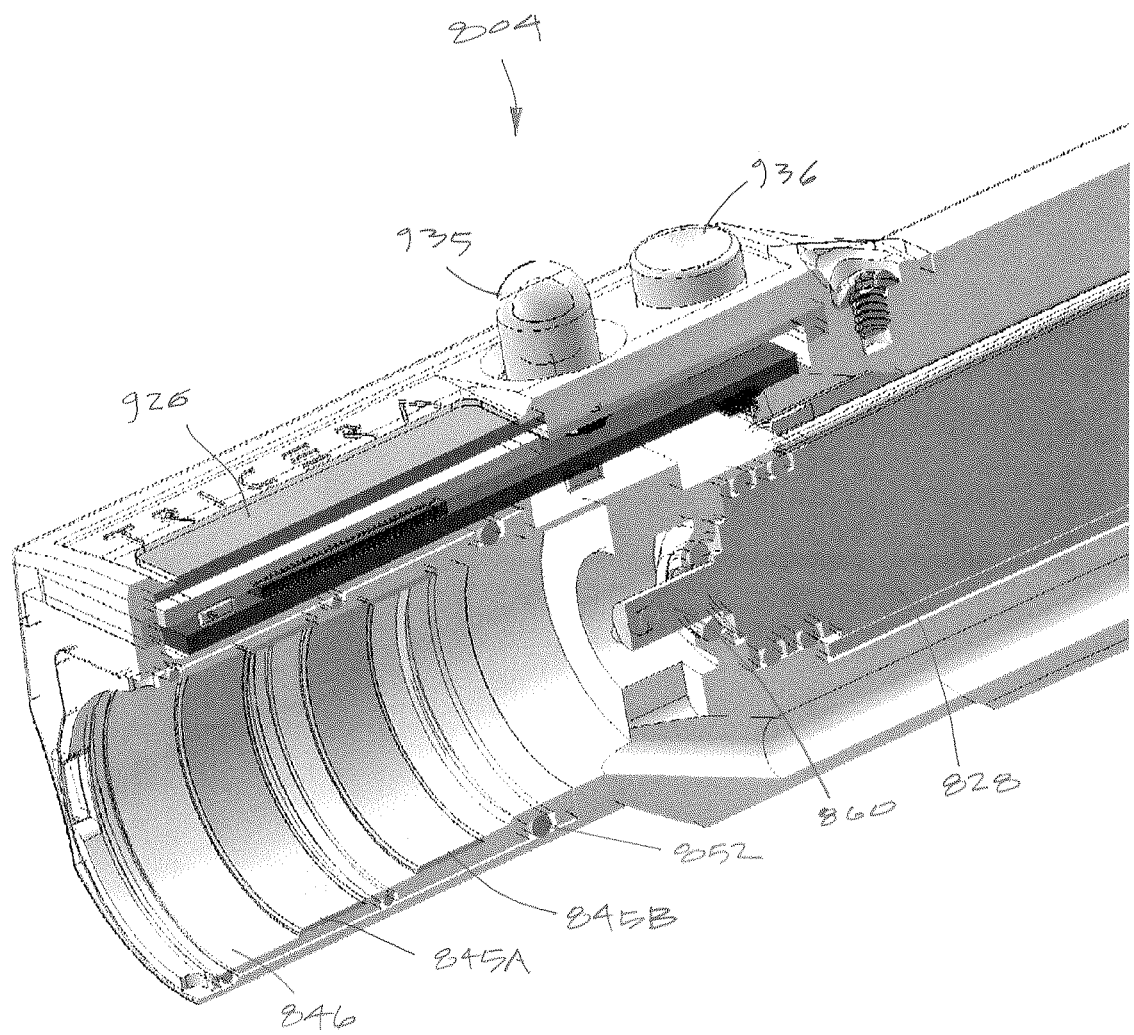
FIG. 19 is an enlarged sectional view of the distal end of the handle of FIG. 18 showing first and second electrical contacts therein for coupling RF energy to a disposable RF probe.
Figure 20:
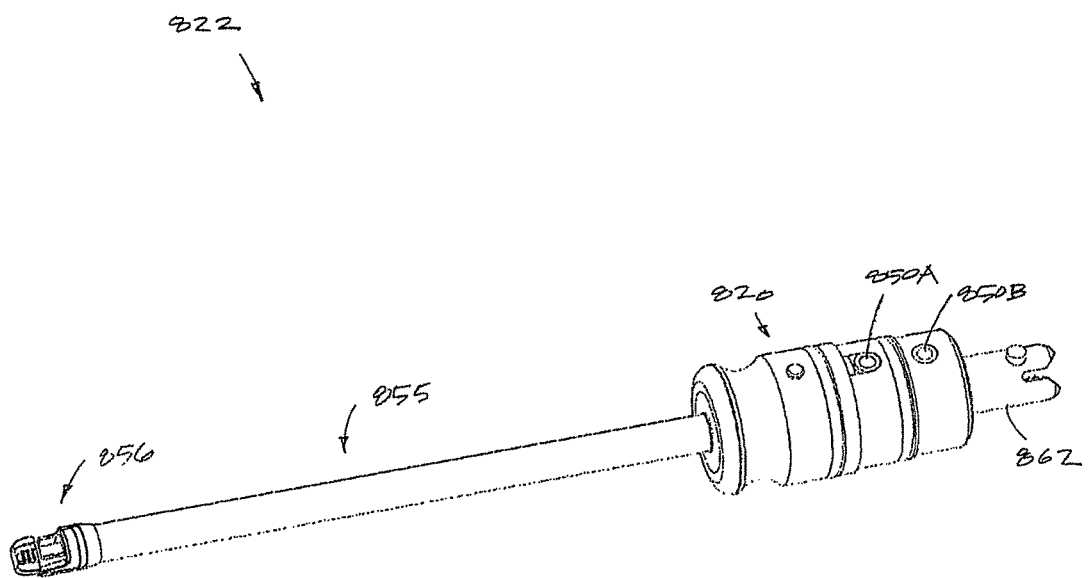
FIG. 20 is a perspective view of a disposable RF probe of the type that couples to the re-useable handle of FIGS. 18-19.

FIGS. 18-21 illustrate components of an arthroscopic system 800 including a re-usable handle 804 that is connected by a single umbilical cable or conduit 805 to a controller unit or console 810. Further, a footswitch 812 is connected by cable 814 to the console 810 for operating the system. As can be seen in FIGS. 18 and 20, the handle 804 is adapted to receive a proximal housing or hub 820 of a disposable RF shaver or probe 822 with RF functionality of the types shown in FIGS. 9-17 above.

In one variation, the console 810 of FIG. 18 includes an electrical power source 825 for operating the motor drive unit 828 in the handle 804, an RF power supply or source 830 for delivering RF energy to the RF electrodes of the disposable RF cutter or shaver 822, and dual peristaltic pumps 835A and 835B for operating the fluid management component of the system. The console 810 further carries a microprocessor or controller 838 with software to operate and integrate all the motor drive, control, and RF functionality of the system. As can be seen in FIG. 18, a disposable cassette 840 carries inflow tubing 842*a* and outflow tubing 842*b* that cooperate with inflow and outflow peristaltic pumps in the console 810. The footswitch 812 in one variation includes switches for operating the motor drive unit 828, for operating the RF probe in a cutting mode with radiofrequency energy, and for operating the RF probe in a coagulation mode.

Figure 21:
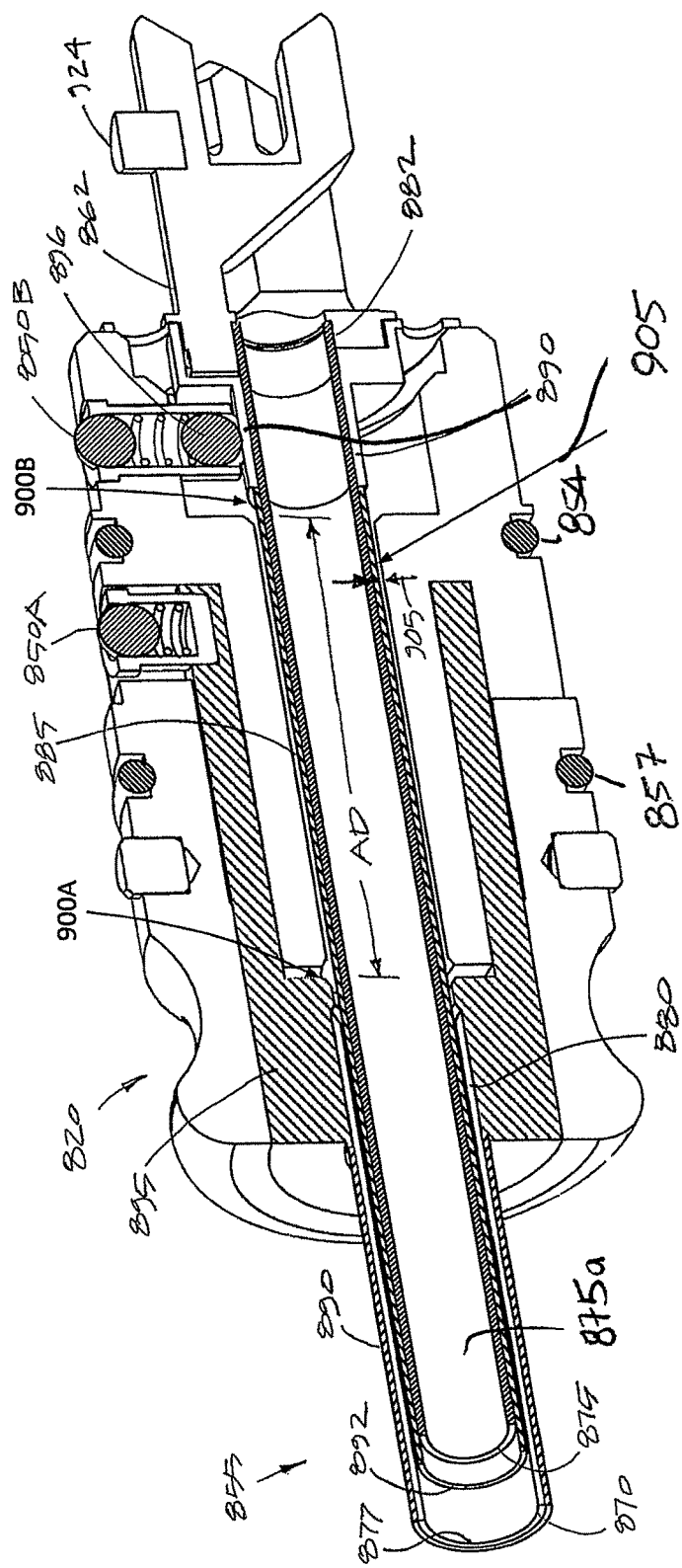
FIG. 21 is a sectional perspective view of a proximal hub portion of the disposable RF probe of FIG. 20.

Of particular interest, the system of the invention includes a handle 804 with first and second electrical contacts 845A and 845B, typically ring-like contacts that form a continuous conductive path circumscribing an inner wall of a receiving passageway 846 of handle 804 (see FIG. 19) that cooperate with electrical contacts 850A and 850B in the proximal hub 820 of the disposable RF shaver 822 (see FIGS. 20-21). In particular, when the proximal hub 820 is fully inserted into the receiving passageway 846, the electrical contacts 850A and 850B will be axially or longitudinally aligned with the electrical contacts 845A and 845B to provide a conductive path to provide RF power from the electrical power source 825 to outer and inner sleeves 870 and 875 of a RF shaver 822, respectively, as will be described further below. The proximal hub 820 can be inserted into the receiving passageway 846 without regard to rotational orientation so that a user can align a working end 856 of a shaft portion 855 of the shaver 822 in any desired relative rotational orientation.

The RF shaver 822 includes the shaft portion 855 that extends to the working end 856 that carries a bi-polar electrode arrangement, of the type shown in FIGS. 9-17. Handle embodiment 804 provides all wiring and circuitry necessary for connecting the RF shaver 822 to the controller 810 within the single umbilical cable or conduit 805 that extends between handle 804 and the console 810. For example, the conduit 805 typically carries electrical power leads for a three-phase motor drive unit 828 in the handle 804, electrical power leads from the RF power supply or source 830 to the handle as well as a number of electrical signal leads for Hall and/or other sensors in the motor drive unit 828 that allow the controller 838 to control the operating parameters of the motor drive 828. In this embodiment, the handle 804 and the conduit 805 are a single component that can be easily sterilized, which is convenient for operating room personnel and economical for hospitals. As can be understood from FIG. 18, the single umbilical cable or conduit 805 is not detachable from the handle 804. In other embodiments, the single umbilical cable or conduit 805 may be detachable from the handle 804.

As described previously with respect to FIGS. 12A-12C, the RF cutter or shaver 22 will typically be connectable to a vacuum or negative pressure source. Preferably, the handle 804 will include a suction port 972 which can be detachably or removably connected to a vacuum or suction line 974 (shown in broken line). A suction lumen 970 extends axially or longitudinally through the handle and has a distal section 976 which connects to the receiving passageway 846 so that a suction or vacuum can be drawn in an inner lumen 875$a$ of the inner sleeve 875 in order to aspirate fluid through the RF shaver when the shaver is connected to the handle, as described elsewhere herein. As a result of this pathway, the electrical contacts 850A and 850B and electrical contacts 845A and 845B may be exposed to the electrically conductive fluids which is being aspirated through the handle. Design aspects of the handle 804 and hub 820 which reduce or eliminate the risk of electrical shorting and/or corrosion resulting from such exposure are described below.

One commercially available RF shaver sold under the tradename DYONICS Bonecutter Electroblade Resector (See, http://www.smith-nephew.com/professional/products/all-products/dyonics-bonecutter-electroblade) utilizes an independent or separate RF electrical cable that carries neither motor power nor electrical signals and couples directly to an exposed part or external surface of the prior art shaver hub. The electrical cable must be routed distally in parallel to a reusable handle. In such a prior art device, the coupling of RF does not extend through the reusable handle.

Figure 22:
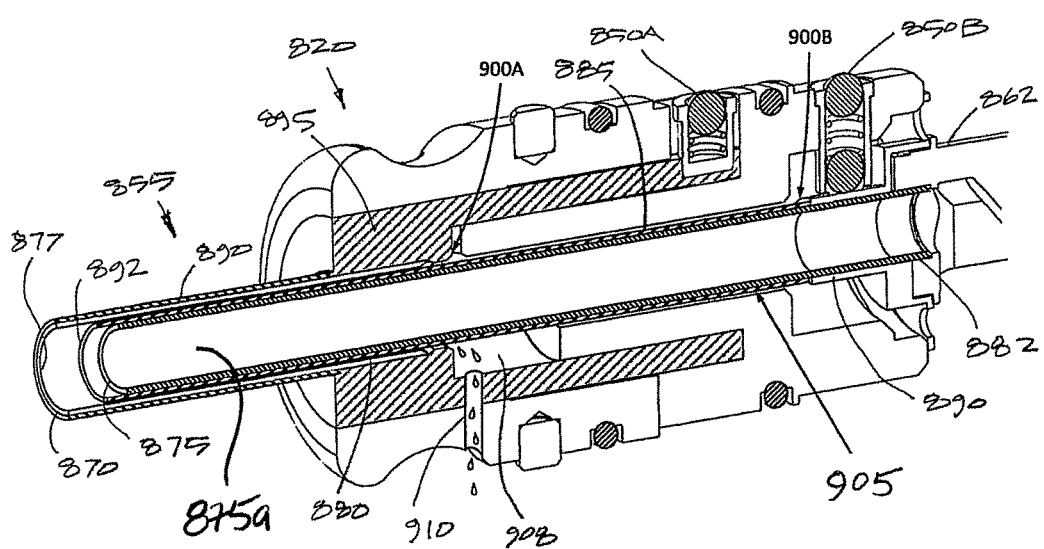
FIG. 22 is a sectional view of a variation of the hub of FIG. 21 which includes a fluid trap for collecting any conductive fluid migrating proximally in the hub.
Figure 23:
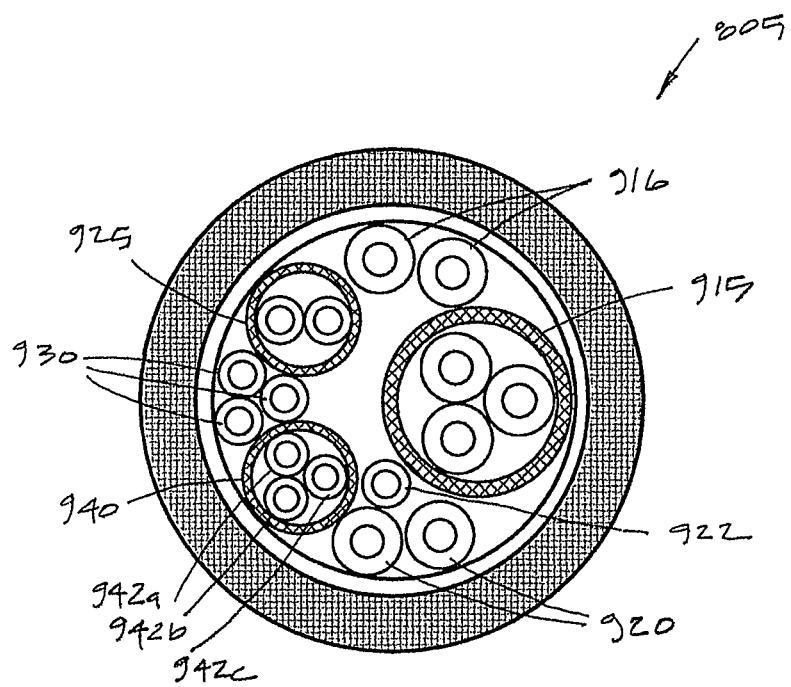
FIG. 23 is a cross-sectional view of the electrical conduit of FIG. 18 taken along line 23-23 of FIG. 18.

The present invention employs a unitary umbilical cable or conduit 805 for coupling the handle 804 to console 810, as shown in FIG. 18. RF power from the handle is supplied to the disposable RF shaver 822 as shown in FIGS. 21-23. The systems of the present invention incorporate a number of innovations for (i) coupling RF energy through the handle to the RF shaver, and (ii) in eliminating electrical interference among sensitive, low power Hall sensor signals and circuitry and the higher power current flows to the motor drive unit 828 and to the RF probe 822.

In one aspect of the invention, referring to FIG. 19, the electrical contacts 845A and 845B are ring-like, e.g. cylindrical or partly cylindrical, typically extending around the inner surface or wall of the receiving passageway 846 of the handle 804. In use, the electrical contacts 845A and 845B will be exposed to electrically conductive fluids and that are aspirated through the probe 822 and outflow passageway or lumen 970 of the handle 804, subjecting the electrical contacts 845A and 845B to alternating current corrosion, which is also known as stray current corrosion, which terms will be used interchangeably herein. Typically, stainless steel would be used for such electrical contacts. However, it has been found that stainless steel electrical contacts would have a very short lifetime in this application due to corrosion during use. As can be understood from FIGS. 19 and 21, the more proximal cylindrical electrical contact 845B in passageway 846 which engages electrical contact 850B in the hub 820 will be exposed fluid outflows, and thus subject to corrosion. The more distal electrical contact 845A in passageway 846 which engages electrical contact 850A in hub 820 is sealed from fluid outflows by O-ring 854 (FIG. 21), but typically the exchange of probes in the handle 804 during a procedure will expose the electrical contact 845A to some conductive fluid which again will result in corrosion, In this application, if stainless steel electrical contacts were used, RF alternating currents that would pass between such stainless steel contact surfaces would consist of a blend of capacitive and resistive current. The resistance between the contacting surfaces of the contacts is referred to as the polarization resistance, which is the transformation resistance that converts electron conductance into current conductance while capacitance makes up the electrochemical layer of the stainless steel surface. The capacitive portion of the current does not lead to corrosion, but causes reduction and oxidation of various chemical species on the metal surface. The resistive part of the current is the part that causes corrosion in the same manner as direct current corrosion. The association between the resistive and capacitive current components is known in alternating current corrosion and such resistance currents can leads to very rapid corrosion.

In one aspect of the invention, to prevent such alternating current corrosion, the electrical contacts 845A and 845B (FIG. 19) in the receiving passageway 846 of the handle 804 comprise materials that resist such corrosion, preferably biocompatible corrosion-resistant materials. By "biocompatible," it is meant that the materials re generally biologically inert and will not cause adverse reactions when exposed to body tissues and fluids under the conditions described herein. In one variation, the first and second electrical contacts 845A and 845B in handle 804 comprise a conductive material selected from the group of titanium, gold, silver, platinum, carbon, molybdenum, tungsten, zinc, Inconel, graphite, nickel or a combination thereof. The first and second electrical contacts 845A and 845B are spaced apart by at least 0.04 inch, often at least 0.08 inch, and sometimes at least 0.16 inch. Such electrical contacts can extend radially at least partly around the cylindrical passageway, or can extend in 360° around the cylindrical passageway 846. The contacts 850A and 850B on the hub 820 can be formed from the same materials but since the disposable RF cutter 822, corrosion is less problematic, so contacts 850A and 850B can also be formed from other materials which are less resistant to alternating current corrosion, such as stainless steel.

In another aspect of the invention, the motor shaft 860 (FIG. 19) will also be exposed to conductive fluids and subject to alternative current corrosion. For this reason, the motor shaft 860 and exposed portions of motor drive unit 828 are comprised of or are plated with, one of the corrosion resistant materials listed above. In one variation, the motor shaft 860 and exposed motor drive components have a surface plating of molybdenum.

In another aspect of the invention, the receiving passageway 846 of the handle 804 includes an O-ring 852 or other fluid seal between the hub 820 and passageway 846, as shown in FIG. 19. Additionally or alternatively, one or more O-rings 854 and 857 or other fluid seals can be carried by the hub 820, as shown in FIG. 21. As can be seen in FIG. 21, one such O-ring 854 can be positioned between the first and second electrical contacts 845A and 845B in the hub 820 and 850A and 850B in the handle to inhibit or prevent any passage of fluid therebetween to reduce the risk of shorting. The second such O-ring 857 can be positioned distally of the electrical contacts, so that together with the O-ring 852 on the receiving passageway 846, seals are provide on proximal and distal sides of the electrical contacts to prevent or inhibit fluid intrusion into annular space between the hub 820 and the surface of passageway 846.

Referring now to FIGS. 20 and 21, another aspect of the invention relates to designs and mechanisms for effectively coupling RF energy from RF power supply or source 830 (FIG. 18) to the working end 856 of the RF probe or cutter 822 through two thin-wall concentric, conductive sleeves 870 and 875 that are assembled into a shaft 855 of the RF probe.

FIG. 21 is an enlarged sectional view of the hub 820 of RF probe 822 which illustrates the components and electrical pathways that enable RF delivery to the probe working end 856. In particular, the shaft 855 comprises an outer sleeve 870 and a concentric inner sleeve 875 that is rotationally disposed in a bore or longitudinal passageway 877 of the outer sleeve 870. Each of the outer sleeve 870 and inner sleeve 875 comprise a thin-wall electrically conductive metal sleeve which carry RF current to and from spaced-apart opposing polarity electrodes in the working end 856. As shown in FIG. 21, the inner sleeve 875 provides an electrically conductive path or conductor to an active electrode in the working end 856, such as a rotatable shaver component as shown, for example, in FIG. 17. In FIG. 21, the outer sleeve 870 is fixed and stationary relative to the hub 820 and has a distal end or region that comprises or serves as a local return or dispersive electrode as is known in the art. A working end with an active electrode and a dispersive or return electrode both located on the cutter or probe will be considered a "bipolar" configuration in contrast to "monopolar" devices which rely on a remote ground or dispersive electrode connected separately to a RF power supply.

As can be seen in FIG. 21, the outer and inner sleeves, 870 and 875, are separated by insulator layers as will be described below. A proximal end 880 of outer sleeve 870 is fixed in the hub 820, for example comprising an electrically non-conductive, plastic material molded over the hub 820. In FIG. 21, a proximal end 882 of the inner sleeve 875 is similarly fixed in a molded plastic coupler 862 that is adapted to mate with a distal end of the shaft 860 of motor drive unit 828 (FIG. 18), typically having spines or other coupling elements to assure sufficient coupling. Thus, the assembly of inner sleeve 875 and the coupler 862 is configured to rotate within a passageway 885 in the hub 820 and within the bore or longitudinal passageway of outer sleeve 870.

The outer sleeve 870 has an exterior insulating layer 890, such as a heat shrink polymer, that extends distally from hub 820 over the shaft 855. The inner sleeve 875 similarly has a heat shrink polymer layer 892 over it outer surface which electrically isolates or separates the inner sleeve 875 from the outer sleeve 870 throughout the length of the shaft 855.

The electrical pathways from the handle 804 to the outer and inner sleeves 870 and 875 are established by the first or proximal-most, spring-loaded electrical contact 850A disposed on an exterior surface of hub 820. The electrical contact 850A is configured to engage the corresponding electrical contact 845A in the handle 804, as shown in FIG. 19 when the hub 820 is fully received in the passageway 846 (FIGS. 18 and 19). The electrical contact 850A is connected and electrically coupled to an electrically conductive core component 895 within the hub 820 that in turn is electrically coupled to a proximal end 880 of the outer sleeve 870.

FIG. 21 further shows a second spring-loaded electrical contact 850B in hub 820 that is adapted to deliver RF current to the rotating inner sleeve 875. In FIG. 21, the electrical contact 850B has a spring-loaded interior portion 896 that engages a collar 890 which in turn is coupled to the inner sleeve 875 and the coupler 862.

Referring still to FIG. 21, an assembly of the hub assembly 820 and the outer sleeve 870 defines a first, proximal-most electrical region, herein called a first polarity region 900A, that is electrically conductively exposed to (i.e. not electrically isolated from) an interior space of the passageway. Similarly, an assembly of the inner sleeve 875 and a collar 890 defines a second polarity region 900B that is electrically conductively exposed to the passageway 885 extending through hub 820.

As the working end 856 of the RF probe or cutter 822 will be immersed a conductive saline or other solution during use, the conductive solution will inevitably migrate, typically by capillary action, in a proximal through an annular space 885 between an inner wall of the bore or longitudinal passageway 877 and an outer wall of the insulator layer 892 over inner sleeve 875. Although this annular space or passageway 885 is very small, saline solution still will migrate over the duration of an arthroscopic procedure, which can be from 5 minutes to an hour or more. As can be understood from FIG. 21, the saline can eventually migrate to form an electrically conductive path or bridge between the first and second opposing polarity regions 900A and 900B. Such bridging would cause a short circuit and disrupt RF current flow between the working end 856 and the RF power supply or source 830. Even if the short-circuit current flow through between regions 900A and 900B is very low and does not stop treatment, it could still cause unwanted heating in interior of hub 820. Thus, it is desirable to limit or eliminate any potential RF current flow between the first and second opposing polarity regions 900A and 900B through the passageway 885 in hub 820.

In one embodiment intended to eliminate such short-circuit RF current flow, shown in FIG. 21, a longitudinal or axial dimension AD between the first and second opposing polarity regions 900A and 900B is selected to be large enough to provide a very high electrical resistance (resistance is proportional to length of the potentially conductive path) in order to substantially or entirely prevent electrical current flow between regions 900A and 900B due. In a variation, the axial dimension AD is at least 0.5 inch, at least 0.6 inch, at least 0.8 inch or at least 1 inch. In such a variation, it is also important to limit the radial dimension of the annular space or gap 905 between the inner and outer sleeves 870 and 875, which can further increases resistance (resistance is inversely proportion to the cross-sectional area of the potential conductive path) to current flow between the first and second opposing polarity regions 900A and 900B. In specific embodiments, the annular gap 905 can have a radial width or dimension of less than 0.006 inch, less than 0.004 inch, or less than 0.002 inch, typically being in a range from 0.001 inch to 0.006 inch, often being in a range from 0.001 inch to 0.004 inch, and sometimes being in a range from 0.001 inch to 0.002 inch. By providing the selected axial dimension AD and radial dimension of the annular gap 905, the potential electrical pathway in a conductive fluid in passageway 885 and any potential unwanted current flow can be substantially reduced and often eliminated.

In other embodiments, other structure or modifications can be provided to reduce or eliminate the amount of conductive saline solution migrating through the annular gap 905 between the opposing polarity regions 900A and 900B. For example, FIG. 22 show an embodiment in which an enlarged annular or partly annular space or fluid trap 908 is provided to allow saline to flow into the space 908 by gravity and collect therein. Such a space will prevent or "break" the capillary action from assisting in the proximal migration of a conductive fluid in passageway 885. In a similar embodiment, still referring to FIG. 22, one or more apertures 910 can be provided in hub 820 to allow any saline in trap 908 to fall outwardly and be removed from the handle 804. In another variation, a desiccant material (not shown) can be exposed to the space 908 to absorb a conductive liquid and thus prevent an electrically conductive pathway between the first and second opposing polarity regions 900A and 900B (see FIG. 22).

As described above, the single umbilical cable or conduit 805 that extends from the handle 804 to console 810 includes multiple electrical cables, wires, or other electrical conductors for powering and operating the motor drive unit 828, for delivering RF energy to the RF probe 822 and for other signaling and control functions as described below. FIG. 23 shows a cross-section of the conduit 805 of FIG. 18.

The single umbilical cable or conduit 805 carries a motor power cable 915 and a RF bipolar cable 916. Cables 920 are provided for power and ground to a circuit board in handle 804. Cable 922 is connected to a Hall sensor (not shown) in handle 804 which detects the rotational position of a magnetic element 924 on coupler 862 (see FIG. 21) which allows the controller to sense the rotational position of coupler 862 and inner sleeve 875 relative to the hub 820. Electrical cable 925 is coupled to the LCD screen 926 in the handle 804 (FIG. 18). Cables indicated at 930 are coupled to the joystick 935 and actuator buttons 936 in the handle 804 as shown in FIG. 18. Finally, a cable 940 has three electrical leads 942a, 942b and 942c that are coupled to three Hall sensors 945a, 945b and 945b in the motor drive unit 828 (FIG. 18) which are adapted to provide signals relating to operating parameters of the motor.

As can be seen in FIG. 18, an interface circuit board 948 in handle 804 carries three Schmitt triggers 950a, 950b and 950c to reduce noise induction on the three independent Hall sensor circuits 945a, 945b, and 945c that are integrated into the three-phase motor 828 in the handle 804. In use, a high fidelity of signals from the Hall sensors 945a, 945b and 945b is essential for controlling the speed and the rotational direction of the three-phase motor. Thus, the three Schmitt triggers 950a, 950b and 950c reduce such noise generated by the three-phase motor.

As signals from the Hall sensors 945a, 945b and 945b travel over the length of the cables 942a, 942b and 942c (see FIG. 23), such signals will couple with the three-phase motor power signals in conduit 805 as well as coupling with RF signals in conduit 805 during use of the RF probe. For this reason, three more Schmitt triggers 960a, 960b and 960c are provided inside the console 810 between the console ends of the Hall sensor circuits and the three-phase motor control circuit (FIG. 18). The role of these three Schmitt triggers 960a, 960b and 960c is to remove this coupled noise before the Hall sensor signals can be routed to control circuitry that controls the three-phase motor 828.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein A number of embodiments of the invention have been described. Nevertheless, it will be understood that various modifications may be made without departing from the spirit and scope of the invention.

What is claimed is:

1. A disposable bipolar RF probe for use in the presence of an electrically conductive fluid, the disposable bipolar RF probe comprising:
   a shaft including an inner electrically conductive sleeve with a first polarity region at a proximal end thereof and an outer electrically conductive sleeve with a second polarity region at a proximal end thereof, wherein the inner electrically conductive sleeve is concentrically received within the outer electrically conductive sleeve along a longitudinal axis, and
   a proximal hub including a central passage, wherein the respective proximal ends of the inner and outer electrically conductive sleeves are received in the central passage such that the first polarity region and the second polarity region are exposed in the central passage and are axially separated from each other in the central passage by an annular space that extends fully from the first polarity region to the second polarity region in the central passage,
   wherein said annular space is open to fluid flow from the first polarity region to the second polarity region to allow the electrically conductive fluid to migrate in a proximal direction through the annular space from the first polarity region to the second polarity region yet has a longitudinal length and a radial dimension selected to achieve an electrical resistance of the electrically conductive fluid along the annular space for limiting current flow between the first polarity region and the second polarity region in the presence of electrically conductive fluid during use.

2. The disposable bipolar RF probe of claim 1, wherein the inner electrically conductive sleeve is configured to couple RF current flow to a first electrode having a first polarity in a working end of the probe, and the outer electrically conductive sleeve is configured to couple RF current flow to a second electrode having a second polarity in the working end of the probe, the first polarity and the second polarity opposing one another.

3. The disposable bipolar RF probe of claim 2, wherein said electrical resistance in the presence of electrically conductive fluid during use is achieved sufficiently so that RF current flow to the working end is unimpeded.

4. The disposable bipolar RF probe of claim 1, wherein at least a portion of the inner electrically conductive sleeve is rotationally disposed in a bore of the outer electrically conductive sleeve.

5. The disposable bipolar RF probe of claim 1, wherein the longitudinal length is at least 0.5 inch.

6. The disposable bipolar RF probe of claim 5, wherein the radial dimension is less than 0.010 inch.

7. The disposable bipolar RF probe of claim 1, wherein the proximal hub is adapted for detachable coupling to a handle carrying first and second electrical contacts for coupling RF current through the proximal hub to said inner and outer electrically conductive sleeves, respectively.

8. A system comprising:
   the disposable bipolar RF probe of claim 1; and
   a handle, wherein the handle includes a motor drive unit for rotating the inner electrically conductive sleeve when the disposable bipolar RF probe is coupled to the handle.

9. The disposable bipolar RF probe of claim 1, wherein the longitudinal length is at least 0.6 inch.

10. The disposable bipolar RF probe of claim 9, wherein the radial dimension is less than 0.004 inch.

11. The disposable bipolar RF probe of claim 9, wherein the radial dimension is less than 0.002 inch.

12. The disposable bipolar RF probe of claim 1, wherein the longitudinal length is at least 0.8 inch.

13. The disposable bipolar RF probe of claim 1, wherein the longitudinal length is at least 1.0 inch.

14. The disposable bipolar RF probe of claim 13, wherein the radial dimension is in the range of 0.001 inch to 0.002 inch.

* * * * *